United States Patent
Robertson et al.

(10) Patent No.: US 8,382,782 B2
(45) Date of Patent: Feb. 26, 2013

(54) ULTRASONIC SURGICAL INSTRUMENTS WITH PARTIALLY ROTATING BLADE AND FIXED PAD ARRANGEMENT

(75) Inventors: Galen C. Robertson, Cincinnati, OH (US); Richard W. Timm, Cincinnati, OH (US); Craig T. Davis, Cincinnati, OH (US); Daniel J. Mumaw, Milford, OH (US); Jerome R. Morgan, Cincinnati, OH (US); Matthew C. Miller, Cincinnati, OH (US); William D. Dannaher, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 290 days.

(21) Appl. No.: 12/703,877

(22) Filed: Feb. 11, 2010

(65) Prior Publication Data
US 2011/0196401 A1    Aug. 11, 2011

(51) Int. Cl.
A61B 17/32    (2006.01)
(52) U.S. Cl. .................................................. 606/169
(58) Field of Classification Search .......... 606/167, 606/169–171, 180; 604/22; 600/562–568
See application file for complete search history.

(56) References Cited

U.S. PATENT DOCUMENTS

| | | | |
|---|---|---|---|
| 2,704,333 A | 3/1955 | Calosi et al. | |
| 2,736,960 A | 3/1956 | Armstrong | |
| 2,849,788 A | 9/1958 | Creek | |
| RE25,033 E | 8/1961 | Balamuth et al. | |
| 3,015,961 A | 1/1962 | Roney | |
| 3,513,848 A | 5/1970 | Winston et al. | |
| 3,526,219 A | 9/1970 | Balamuth | |
| 3,614,484 A | 10/1971 | Shoh | |
| 3,636,943 A | 1/1972 | Balamuth | |
| 3,776,238 A | 12/1973 | Peyman et al. | |
| 3,805,787 A | 4/1974 | Banko | |
| 3,830,098 A | 8/1974 | Antonevich | |
| 3,854,737 A | 12/1974 | Gilliam, Sr. | |
| 3,862,630 A | 1/1975 | Balamuth | |
| 3,900,823 A | 8/1975 | Sokal et al. | |
| 3,918,442 A | 11/1975 | Nikolaev et al. | |
| 3,946,738 A | 3/1976 | Newton et al. | |
| 3,955,859 A | 5/1976 | Stella et al. | |

(Continued)

FOREIGN PATENT DOCUMENTS

| CN | 1634601 A | 7/2005 |
|---|---|---|
| CN | 1640365 A | 7/2005 |

(Continued)

OTHER PUBLICATIONS

Technology Overview, printed from www.harmonicscalpel.com, Internet site, website accessed on Jun. 13, 2007, (3 pages).

(Continued)

*Primary Examiner* — Ryan Severson

(57) ABSTRACT

An ultrasonic surgical instrument that supports an ultrasonically excited blade and an outer sheath that can be selectively rotated relative to each other to bring a distal cutting tip of the blade into contact with at least one cutting surface formed on a distal end of the outer sheath. In some embodiments, the distal cutting tip may contact two cutting surfaces located on opposing sides of an opening in the outer sheath through which the distal cutting tip protrudes. Tissue pads may be attached to the cutting surfaces. Various embodiments also include at least one suction lumen.

20 Claims, 15 Drawing Sheets

U.S. PATENT DOCUMENTS

| | | |
|---|---|---|
| 3,956,826 A | 5/1976 | Perdreaux, Jr. |
| 4,156,187 A | 5/1979 | Murry et al. |
| 4,188,927 A | 2/1980 | Harris |
| 4,200,106 A | 4/1980 | Douvas et al. |
| 4,306,570 A | 12/1981 | Matthews |
| 4,445,063 A | 4/1984 | Smith |
| 4,491,132 A | 1/1985 | Aikins |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,649,919 A * | 3/1987 | Thimsen et al. ............... 606/80 |
| 4,708,127 A | 11/1987 | Abdelghani |
| 4,712,722 A | 12/1987 | Hood et al. |
| 4,827,911 A | 5/1989 | Broadwin et al. |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,903,696 A | 2/1990 | Stasz et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,126,618 A | 6/1992 | Takahashi et al. |
| 5,162,044 A | 11/1992 | Gahn et al. |
| 5,167,725 A | 12/1992 | Clark et al. |
| 332,660 A | 1/1993 | Rawson et al. |
| 5,176,695 A | 1/1993 | Dulebohn |
| 5,184,605 A | 2/1993 | Grezeszykowski |
| 5,213,569 A | 5/1993 | Davis |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,275,609 A | 1/1994 | Pingleton et al. |
| 5,282,800 A | 2/1994 | Foshee et al. |
| 5,304,115 A | 4/1994 | Pflueger et al. |
| 347,474 A | 5/1994 | Olson |
| 5,322,055 A | 6/1994 | Davison et al. |
| 5,324,299 A | 6/1994 | Davison et al. |
| 5,344,420 A | 9/1994 | Hilal et al. |
| 5,346,502 A | 9/1994 | Estabrook et al. |
| 5,357,423 A | 10/1994 | Weaver et al. |
| 5,366,466 A | 11/1994 | Christian et al. |
| 354,564 A | 1/1995 | Medema |
| 5,381,067 A | 1/1995 | Greenstein et al. |
| 5,403,312 A | 4/1995 | Yates et al. |
| 5,411,481 A | 5/1995 | Allen et al. |
| 5,419,761 A | 5/1995 | Narayanan et al. |
| 5,421,829 A | 6/1995 | Olichney et al. |
| 5,438,997 A | 8/1995 | Sieben et al. |
| 5,449,370 A | 9/1995 | Vaitekunas |
| 5,471,988 A | 12/1995 | Fujio et al. |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,527,331 A | 6/1996 | Kresch et al. |
| 5,562,609 A | 10/1996 | Brumbach |
| 5,562,610 A | 10/1996 | Brumbach |
| 5,601,601 A | 2/1997 | Tal et al. |
| 5,603,773 A | 2/1997 | Campbell |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| 381,077 A | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,730,752 A | 3/1998 | Alden et al. |
| 5,733,074 A | 3/1998 | Stöck et al. |
| 5,741,226 A | 4/1998 | Strukel et al. |
| 5,792,135 A | 8/1998 | Madhani et al. |
| 5,810,859 A | 9/1998 | DiMatteo et al. |
| 5,817,084 A | 10/1998 | Jensen |
| 5,827,323 A | 10/1998 | Klieman et al. |
| 5,828,160 A | 10/1998 | Sugishita |
| 5,836,897 A | 11/1998 | Sakurai et al. |
| 5,843,109 A | 12/1998 | Mehta et al. |
| 5,878,193 A | 3/1999 | Wang et al. |
| 5,879,364 A | 3/1999 | Bromfield et al. |
| 5,893,835 A | 4/1999 | Witt et al. |
| 5,897,569 A | 4/1999 | Kellogg et al. |
| 5,906,628 A | 5/1999 | Miyawaki et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 416,089 A | 11/1999 | Barton et al. |
| 5,980,510 A | 11/1999 | Tsonton et al. |
| 5,989,274 A | 11/1999 | Davison et al. |
| 5,989,275 A | 11/1999 | Estabrook et al. |
| 5,993,972 A | 11/1999 | Reich et al. |
| 6,024,741 A | 2/2000 | Williamson, IV et al. |
| 6,033,375 A | 3/2000 | Brumbach |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,110,127 A | 8/2000 | Suzuki |
| 6,113,594 A | 9/2000 | Savage |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,152,902 A | 11/2000 | Christian et al. |
| 6,159,160 A | 12/2000 | Hsei et al. |
| 6,159,175 A | 12/2000 | Strukel et al. |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |

| | | | | | | | |
|---|---|---|---|---|---|---|---|
| 6,325,811 | B1 | 12/2001 | Messerly | D511,145 | S | 11/2005 | Donofrio et al. |
| 6,328,751 | B1 | 12/2001 | Beaupre | 6,976,844 | B2 | 12/2005 | Hickok et al. |
| 6,340,352 | B1 | 1/2002 | Okada et al. | 6,976,969 | B2 | 12/2005 | Messerly |
| 6,352,532 | B1 | 3/2002 | Kramer et al. | 6,977,495 | B2 | 12/2005 | Donofrio |
| 6,364,888 | B1 | 4/2002 | Niemeyer et al. | 6,984,220 | B2 | 1/2006 | Wuchinich |
| 6,379,320 | B1 | 4/2002 | Lafon et al. | 7,011,657 | B2 | 3/2006 | Truckai et al. |
| D457,958 | S | 5/2002 | Dycus et al. | 7,041,083 | B2 | 5/2006 | Chu et al. |
| 6,383,194 | B1 | 5/2002 | Pothula | 7,041,088 | B2 | 5/2006 | Nawrocki et al. |
| 6,387,109 | B1 | 5/2002 | Davison et al. | 7,041,102 | B2 | 5/2006 | Truckai et al. |
| 6,388,657 | B1 | 5/2002 | Natoli | 7,070,597 | B2 | 7/2006 | Truckai et al. |
| 6,391,042 | B1 | 5/2002 | Cimino | 7,074,219 | B2 | 7/2006 | Levine et al. |
| 6,405,733 | B1 | 6/2002 | Fogarty et al. | 7,077,039 | B2 | 7/2006 | Gass et al. |
| 6,416,486 | B1 | 7/2002 | Wampler | 7,077,853 | B2 | 7/2006 | Kramer et al. |
| 6,423,073 | B2 | 7/2002 | Bowman | 7,083,619 | B2 | 8/2006 | Truckai et al. |
| 6,423,082 | B1 | 7/2002 | Houser et al. | 7,087,054 | B2 | 8/2006 | Truckai et al. |
| 6,428,539 | B1 * | 8/2002 | Baxter et al. ................... 606/49 | 7,101,378 | B2 * | 9/2006 | Salameh et al. ............. 606/113 |
| 6,432,118 | B1 | 8/2002 | Messerly | 7,108,695 | B2 | 9/2006 | Witt et al. |
| 6,436,114 | B1 | 8/2002 | Novak et al. | 7,112,201 | B2 | 9/2006 | Truckai et al. |
| 6,436,115 | B1 | 8/2002 | Beaupre | 7,118,564 | B2 | 10/2006 | Ritchie et al. |
| 6,443,969 | B1 | 9/2002 | Novak et al. | 7,124,932 | B2 | 10/2006 | Isaacson et al. |
| 6,454,781 | B1 | 9/2002 | Witt et al. | 7,125,409 | B2 | 10/2006 | Truckai et al. |
| 6,454,782 | B1 | 9/2002 | Schwemberger | 7,135,018 | B2 | 11/2006 | Ryan et al. |
| 6,458,142 | B1 | 10/2002 | Faller et al. | 7,135,030 | B2 | 11/2006 | Schwemberger et al. |
| 6,480,796 | B2 | 11/2002 | Wiener | 7,153,315 | B2 | 12/2006 | Miller |
| 6,485,490 | B2 | 11/2002 | Wampler et al. | D536,093 | S | 1/2007 | Nakajima et al. |
| 6,491,708 | B2 | 12/2002 | Madan et al. | 7,156,189 | B1 | 1/2007 | Bar-Cohen et al. |
| 6,497,715 | B2 | 12/2002 | Satou | 7,156,853 | B2 | 1/2007 | Muratsu |
| 6,500,176 | B1 | 12/2002 | Truckai et al. | 7,157,058 | B2 | 1/2007 | Marhasin et al. |
| 6,500,188 | B2 | 12/2002 | Harper et al. | 7,159,750 | B2 | 1/2007 | Racenet et al. |
| 6,524,316 | B1 | 2/2003 | Nicholson et al. | 7,163,548 | B2 | 1/2007 | Stulen et al. |
| 6,527,736 | B1 | 3/2003 | Attinger et al. | 7,169,146 | B2 | 1/2007 | Truckai et al. |
| 6,533,784 | B2 | 3/2003 | Truckai et al. | 7,179,271 | B2 | 2/2007 | Friedman et al. |
| 6,537,291 | B2 | 3/2003 | Friedman et al. | 7,186,253 | B2 | 3/2007 | Truckai et al. |
| 6,543,452 | B1 | 4/2003 | Lavigne | 7,189,233 | B2 | 3/2007 | Truckai et al. |
| 6,543,456 | B1 | 4/2003 | Freeman | 7,204,820 | B2 | 4/2007 | Akahoshi |
| 6,544,260 | B1 | 4/2003 | Markel et al. | 7,220,951 | B2 | 5/2007 | Truckai et al. |
| 6,561,983 | B2 | 5/2003 | Cronin et al. | 7,223,229 | B2 | 5/2007 | Inman et al. |
| 6,572,632 | B2 | 6/2003 | Zisterer et al. | 7,229,455 | B2 | 6/2007 | Sakurai et al. |
| 6,575,969 | B1 | 6/2003 | Rittman, III et al. | 7,273,483 | B2 | 9/2007 | Wiener et al. |
| 6,582,451 | B1 | 6/2003 | Marucci et al. | 7,309,849 | B2 | 12/2007 | Truckai et al. |
| 6,589,200 | B1 | 7/2003 | Schwemberger et al. | 7,311,709 | B2 | 12/2007 | Truckai et al. |
| 6,589,239 | B2 | 7/2003 | Khandkar et al. | 7,317,955 | B2 | 1/2008 | McGreevy |
| 6,616,450 | B2 | 9/2003 | Mossle | 7,326,236 | B2 | 2/2008 | Andreas et al. |
| 6,623,501 | B2 | 9/2003 | Heller et al. | 7,331,410 | B2 | 2/2008 | Yong et al. |
| 6,626,926 | B2 | 9/2003 | Friedman et al. | 7,353,068 | B2 | 4/2008 | Tanaka et al. |
| 6,633,234 | B2 | 10/2003 | Wiener et al. | 7,354,440 | B2 | 4/2008 | Truckai et al. |
| 6,656,177 | B2 | 12/2003 | Truckai et al. | 7,380,695 | B2 | 6/2008 | Doll et al. |
| 6,662,127 | B2 | 12/2003 | Wiener et al. | 7,380,696 | B2 | 6/2008 | Shelton, IV et al. |
| 6,663,941 | B2 | 12/2003 | Brown et al. | 7,381,209 | B2 | 6/2008 | Truckai et al. |
| 6,669,690 | B1 | 12/2003 | Okada et al. | 7,390,317 | B2 | 6/2008 | Taylor et al. |
| 6,676,660 | B2 | 1/2004 | Wampler et al. | 7,404,508 | B2 | 7/2008 | Smith et al. |
| 6,678,621 | B2 | 1/2004 | Wiener et al. | 7,408,288 | B2 | 8/2008 | Hara |
| 6,679,899 | B2 | 1/2004 | Wiener et al. | D576,725 | S | 9/2008 | Shumer et al. |
| 6,682,544 | B2 | 1/2004 | Mastri et al. | D578,643 | S | 10/2008 | Shumer et al. |
| 6,689,146 | B1 | 2/2004 | Himes | D578,644 | S | 10/2008 | Shumer et al. |
| 6,716,215 | B1 | 4/2004 | David et al. | D578,645 | S | 10/2008 | Shumer et al. |
| 6,731,047 | B2 | 5/2004 | Kauf et al. | 7,431,704 | B2 | 10/2008 | Babaev |
| 6,733,506 | B1 | 5/2004 | McDevitt et al. | 7,441,684 | B2 | 10/2008 | Shelton, IV et al. |
| 6,762,535 | B2 | 7/2004 | Take et al. | 7,455,208 | B2 | 11/2008 | Wales et al. |
| 6,770,072 | B1 | 8/2004 | Truckai et al. | 7,472,815 | B2 | 1/2009 | Shelton, IV et al. |
| 6,773,443 | B2 | 8/2004 | Truwit et al. | 7,479,148 | B2 | 1/2009 | Beaupre |
| 6,773,444 | B2 | 8/2004 | Messerly | 7,479,160 | B2 | 1/2009 | Branch et al. |
| 6,783,524 | B2 | 8/2004 | Anderson et al. | 7,494,468 | B2 | 2/2009 | Rabiner et al. |
| 6,786,382 | B1 | 9/2004 | Hoffman | 7,503,893 | B2 | 3/2009 | Kucklick |
| 6,786,383 | B2 | 9/2004 | Stegelmann | 7,506,790 | B2 | 3/2009 | Shelton, IV |
| 6,790,216 | B1 | 9/2004 | Ishikawa | 7,506,791 | B2 | 3/2009 | Omaits et al. |
| 6,802,843 | B2 | 10/2004 | Truckai et al. | 7,524,320 | B2 | 4/2009 | Tierney et al. |
| 6,828,712 | B2 | 12/2004 | Battaglin et al. | 7,534,243 | B1 | 5/2009 | Chin et al. |
| 6,869,439 | B2 | 3/2005 | White et al. | D594,983 | S | 6/2009 | Price et al. |
| 6,875,220 | B2 | 4/2005 | Du et al. | 7,549,564 | B2 | 6/2009 | Boudreaux |
| 6,905,497 | B2 | 6/2005 | Truckai et al. | 7,559,450 | B2 | 7/2009 | Wales et al. |
| 6,908,472 | B2 | 6/2005 | Wiener et al. | 7,567,012 | B2 | 7/2009 | Namikawa |
| 6,913,579 | B2 | 7/2005 | Truckai et al. | 7,654,431 | B2 | 2/2010 | Hueil et al. |
| 6,926,716 | B2 | 8/2005 | Baker et al. | 7,665,647 | B2 | 2/2010 | Shelton, IV et al. |
| 6,929,632 | B2 | 8/2005 | Nita et al. | 7,670,334 | B2 | 3/2010 | Hueil et al. |
| 6,929,644 | B2 | 8/2005 | Truckai et al. | 7,674,263 | B2 | 3/2010 | Ryan |
| D509,589 | S | 9/2005 | Wells | 7,691,098 | B2 | 4/2010 | Wallace et al. |
| 6,942,677 | B2 | 9/2005 | Nita et al. | 7,713,202 | B2 | 5/2010 | Boukhny et al. |
| 6,945,981 | B2 | 9/2005 | Donofrio et al. | 7,714,481 | B2 | 5/2010 | Sakai |

| | | |
|---|---|---|
| D618,797 S | 6/2010 | Price et al. |
| 7,751,115 B2 | 7/2010 | Song |
| 7,770,774 B2 | 8/2010 | Mastri et al. |
| 7,770,775 B2 | 8/2010 | Shelton, IV et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,806,891 B2 | 10/2010 | Nowlin et al. |
| 7,810,693 B2 | 10/2010 | Broehl et al. |
| 7,824,401 B2 | 11/2010 | Manzo et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,959,050 B2 | 6/2011 | Smith et al. |
| 7,959,626 B2 | 6/2011 | Hong et al. |
| 7,976,544 B2 | 7/2011 | McClurken et al. |
| 8,038,693 B2 | 10/2011 | Allen |
| 8,061,014 B2 | 11/2011 | Smith et al. |
| 8,089,197 B2 | 1/2012 | Rinner et al. |
| 8,157,145 B2 | 4/2012 | Shelton, IV et al. |
| 8,162,966 B2 | 4/2012 | Connor et al. |
| 8,177,800 B2 | 5/2012 | Spitz et al. |
| 8,182,502 B2 | 5/2012 | Stulen et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,253,303 B2 | 8/2012 | Giordano et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0077550 A1 | 6/2002 | Rabiner et al. |
| 2002/0156493 A1 | 10/2002 | Houser et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2003/0212422 A1 | 11/2003 | Fenton et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0102772 A1* | 5/2004 | Baxter et al. .................. 606/45 |
| 2004/0199193 A1 | 10/2004 | Hayashi et al. |
| 2004/0204728 A1 | 10/2004 | Haefner |
| 2004/0260300 A1 | 12/2004 | Gorensek et al. |
| 2005/0033337 A1 | 2/2005 | Muir et al. |
| 2005/0049546 A1 | 3/2005 | Messerly et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0079878 A1 | 4/2006 | Houser |
| 2006/0084963 A1 | 4/2006 | Messerly |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143795 A1 | 6/2009 | Robertson |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0270853 A1 | 10/2009 | Yachi et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0036405 A1 | 2/2010 | Giordano et al. |
| 2010/0069940 A1 | 3/2010 | Miller et al. |
| 2010/0158307 A1 | 6/2010 | Kubota et al. |
| 2010/0179577 A1 | 7/2010 | Houser |
| 2010/0187283 A1 | 7/2010 | Crainich et al. |

| | | | |
|---|---|---|---|
| 2010/0193567 A1 | 8/2010 | Scheib et al. | |
| 2010/0298743 A1 | 11/2010 | Nield et al. | |
| 2010/0298851 A1 | 11/2010 | Nield | |
| 2010/0331869 A1 | 12/2010 | Voegele et al. | |
| 2010/0331870 A1 | 12/2010 | Wan et al. | |
| 2010/0331871 A1 | 12/2010 | Nield et al. | |
| 2010/0331872 A1 | 12/2010 | Houser et al. | |
| 2011/0009850 A1 | 1/2011 | Main et al. | |
| 2011/0015627 A1 | 1/2011 | DiNardo et al. | |
| 2011/0015631 A1 | 1/2011 | Wiener et al. | |
| 2011/0015660 A1 | 1/2011 | Wiener et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087218 A1 | 4/2011 | Boudreaux et al. | |
| 2011/0087256 A1 | 4/2011 | Wiener et al. | |
| 2011/0196286 A1 | 8/2011 | Robertson et al. | |
| 2011/0196287 A1 | 8/2011 | Robertson et al. | |
| 2011/0196398 A1 | 8/2011 | Robertson et al. | |
| 2011/0196399 A1 | 8/2011 | Robertson et al. | |
| 2011/0196400 A1 | 8/2011 | Robertson et al. | |
| 2011/0196402 A1 | 8/2011 | Robertson et al. | |
| 2011/0196403 A1 | 8/2011 | Robertson et al. | |
| 2011/0196404 A1 | 8/2011 | Dietz et al. | |
| 2011/0196405 A1 | 8/2011 | Dietz | |
| 2011/0288452 A1 | 11/2011 | Houser et al. | |
| 2012/0029546 A1 | 2/2012 | Robertson | |
| 2012/0059289 A1 | 3/2012 | Nield et al. | |
| 2012/0078139 A1 | 3/2012 | Aldridge et al. | |
| 2012/0078247 A1 | 3/2012 | Worrell et al. | |
| 2012/0083783 A1 | 4/2012 | Davison et al. | |
| 2012/0083784 A1 | 4/2012 | Davison et al. | |
| 2012/0184946 A1 | 7/2012 | Price et al. | |
| 2012/0203257 A1 | 8/2012 | Stulen et al. | |

FOREIGN PATENT DOCUMENTS

| | | |
|---|---|---|
| CN | 1694649 A | 11/2005 |
| CN | 1922563 A | 2/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1433425 B1 | 6/2006 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| GB | 2032221 A | 4/1980 |
| GB | 2447767 B | 8/2011 |
| JP | 6-104503 A | 4/1994 |
| JP | 2005027026 A | 1/2005 |
| JP | 2006217716 A | 8/2006 |
| WO | WO 92/22259 A2 | 12/1992 |
| WO | WO 93/14708 A1 | 8/1993 |
| WO | WO 98/37815 A1 | 9/1998 |
| WO | WO 01/54590 A1 | 8/2001 |
| WO | WO 2005/122917 A1 | 12/2005 |
| WO | WO 2006/042210 A2 | 4/2006 |
| WO | WO 2006/058223 A2 | 6/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/130793 A1 | 10/2008 |
| WO | WO 2009/018406 A2 | 2/2009 |
| WO | WO 2009/027065 A1 | 3/2009 |
| WO | WO 2011/144911 A1 | 11/2011 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.

International Search Report for PCT/US2011/024201, dated Apr. 29, 2011 (5 pages).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gernert, eds., Plenum, New York (1995).

Campbell et al, "Thermal Imaging in Surgery," p. 19-3, in *Medical Infrared Imaging*, N. A. Diakides and J. D. Bronzino, Eds. (2008).

* cited by examiner

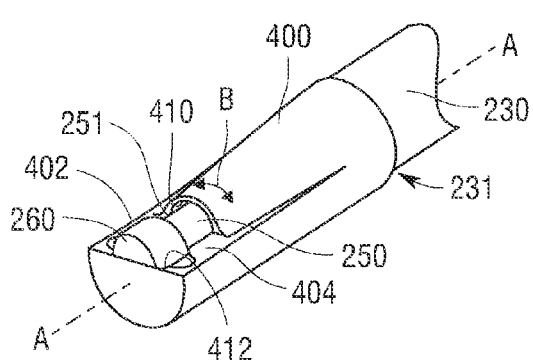
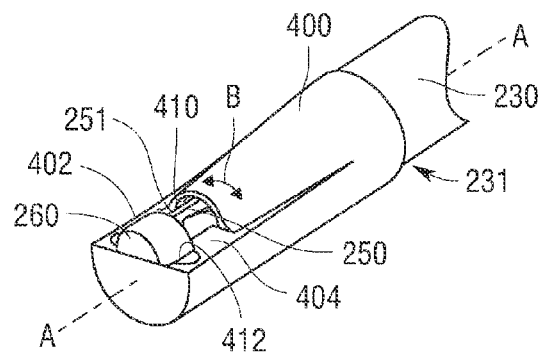
*Fig. 6*   *Fig. 7*
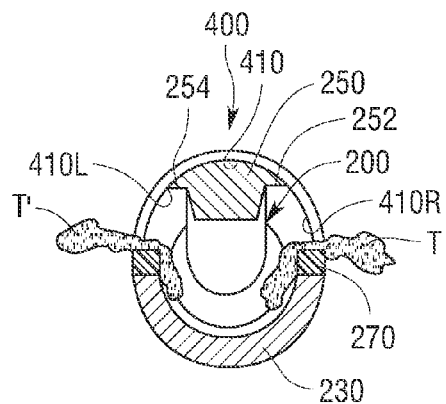
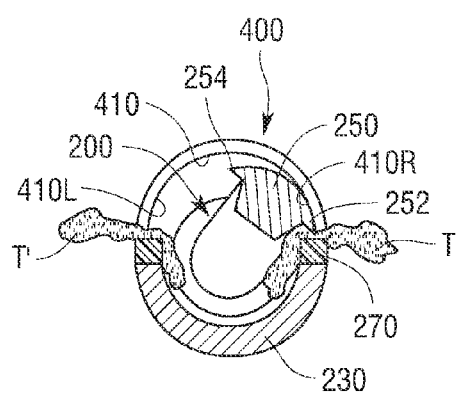
*Fig. 8A*   *Fig. 8B*
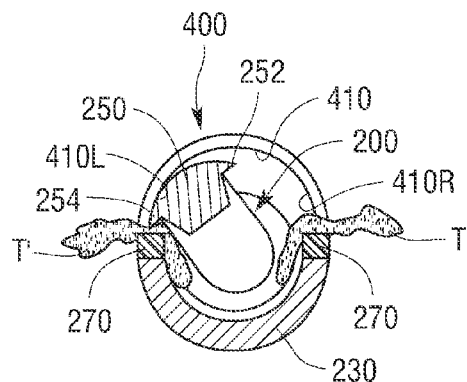
*Fig. 8C*

ULTRASONIC SURGICAL INSTRUMENTS WITH PARTIALLY ROTATING BLADE AND FIXED PAD ARRANGEMENT

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. These devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. In addition, such device may employ a suction channel that travels through the interior of the inner tube. For example, U.S. Pat. No. 4,850,354 to McGurk-Burleson, et al., discloses a non-ultrasonically powered surgical cutting instrument that comprises a rotary cutter for cutting material with a shearing action. It employs an inner cutting member which is rotatable within an outer tube.

U.S. Pat. No. 3,776,238 to Peyman et al. discloses an ophthalmic instrument in which tissue is cut by a chopping action set-up by the sharp end of an inner tube moving against the inner surface of the end of an outer tube. U.S. Pat. No. 5,226,910 to Kajiyama et al. discloses another surgical cutting instrument that has an inner member which moves relative to an outer member to cut tissue entering through an aperture in the outer member.

U.S. Pat. No. 4,922,902 to Wuchinich et al. discloses a method and apparatus for endoscopic removal of tissue utilizing an ultrasonic aspirator. The device uses an ultrasonic probe which disintegrates compliant tissue and aspirates it through a narrow orifice. U.S. Pat. No. 4,634,420 to Spinosa et al. discloses an apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle. U.S. Pat. No. 3,805,787 to Banko discloses yet another ultrasonic instrument that has a probe that is shielded to narrow the beam of ultrasonic energy radiated from the tip of the probe. In one embodiment the shield extends past the free-end of the probe to prevent the probe from coming into contact with the tissue. U.S. Pat. No. 5,213,569 to Davis discloses a phaco-emulsification needle which focuses the ultrasonic energy. The focusing surfaces can be beveled, curved or faceted. U.S. Pat. No. 6,984,220 to Wuchinich and U.S. Patent Publication No. US 2005/0177184 to Easley disclose ultrasonic tissue dissection systems that provide combined longitudinal and torsional motion through the use of longitudinal-torsional resonators. U.S Patent Publication no. US 2006/0030797 A1 to Zhou et al. discloses an orthopedic surgical device that has a driving motor for driving an ultrasound transducer and horn. An adapter is provided between the driving motor and transducer for supplying ultrasonic energy signals to the transducer.

There is a need for a surgical instrument that can cut and remove tissue rapidly and hemostatically in an arthroscopic environment.

The foregoing discussion is intended only to illustrate some of the shortcomings present in the field of the invention at the time, and should not be taken as a disavowal of claim scope.

SUMMARY

In one general aspect, various embodiments are directed to an ultrasonic surgical instrument that includes a housing that supports an outer sheath. The outer sheath may have a distal blade opening therein that defines at least one cutting surface. The outer sheath may further have at least one suction lumen therethrough that communicates with the distal blade opening. An ultrasonic transducer assembly may be supported by the housing and have a blade coupled thereto. The blade may extend through the outer sheath such that a distal tip of the blade extends into the blade opening. A tissue cutting portion of the distal tip of the blade may protrude radially out of the blade opening. A motor may be supported by the housing and be coupled to one of the ultrasonic transducer assembly and the outer sheath for applying rotational motion thereto such that the tissue cutting portion of the blade is brought into contact with the one cutting surface on the outer sheath.

In connection with another general aspect of the present invention, there is provided a method of cutting tissue. In one form, the method comprises inserting a blade of a surgical instrument into a patient wherein the blade is attached to a source of ultrasonic motion and extends through a hollow outer sheath such that a tissue cutting tip of the blade is exposed through a blade opening in the outer sheath. One of the blade and outer sheath is selectively rotatable relative to the other. The method may further include positioning the blade and outer sheath such that the blade opening is adjacent to target tissue within the patient and applying suction through the outer sheath to draw target tissue into the blade opening. The method may also include oscillating one of the blade and outer sheath relative to the other such that the tissue cutting tip of the blade contacts and traps a portion of the target tissue drawn into the blade opening between the cutting tip and a cutting surface on the outer sheath.

In connection with yet another general aspect of the present invention there is provided an ultrasonic surgical instrument that includes a housing that supports an outer sheath. The outer sheath may have distal blade opening therein that defines at least one cutting surface. An ultrasonic transducer assembly may be rotatably supported by the housing. A blade may be coupled to the ultrasonic transducer assembly and extend through the outer sheath such that a distal tip of the blade extends into the distal blade opening wherein a tissue cutting portion thereof protrudes radially out of the distal blade opening. A motor may be supported by the housing and be coupled to the ultrasonic transducer assembly for applying rotational motion thereto such that the tissue cutting portion of the blade is brought into contact with the at least one cutting surface. The instrument may further include means for limiting an amount of torsion experienced by the tissue cutting portion of said blade when in contact with the cutting surface.

FIGURES

The features of various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 6 is a perspective view of a portion of a non-limiting outer sheath and distal sheath tip embodiment of the present invention with the tissue cutting tip of the blade in one position;

FIG. 7 is another perspective view of the outer sheath and distal sheath tip embodiment of FIG. 6 with the blade in another position;

FIG. 8A is a partial cross-sectional end view of the outer sheath and blade arrangement of FIGS. 6 and 7 with the blade in a central position;

FIG. 8B is another partial cross-sectional end view of the outer sheath and blade arrangement of FIG. 8A with the blade in a tissue cutting position;

FIG. 8C is another partial cross-sectional end view of the outer sheath and blade arrangement of FIGS. 8A and 8B with the blade in another tissue cutting position;

DESCRIPTION

Figure 1:
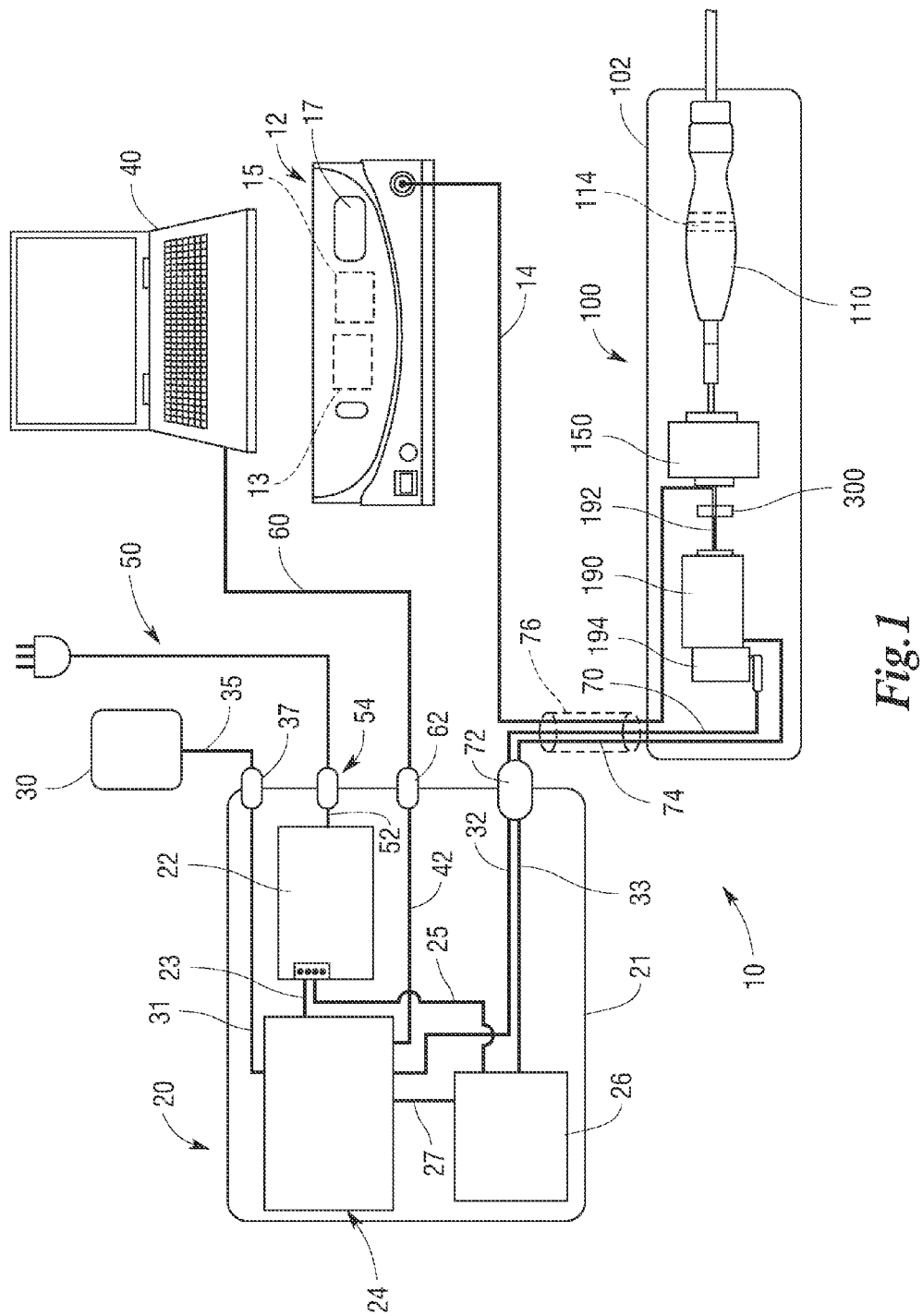
FIG. 1 is a schematic view of a non-limiting surgical control system embodiment of the present invention.

The owner of the present application also owns the following U.S. Patent Applications that were filed on even date herewith and which are herein incorporated by reference in their respective entireties:

U.S. patent application Ser. No. 12/703,860, entitled ULTRASONICALLY POWERED SURGICAL INSTRUMENTS WITH ROTATING CUTTING IMPLEMENT;

U.S. patent application Ser. No. 12/703,864, entitled METHODS OF USING ULTRASONICALLY POWERED SURGICAL INSTRUMENTS WITH ROTATABLE CUTTING IMPLEMENTS;

U.S. patent application Ser. No. 12/703,866, entitled SEAL ARRANGEMENTS FOR ULTRASONICALLY POWERED SURGICAL INSTRUMENTS;

U.S. patent application Ser. No. 12/703,870, entitled ULTRASONIC SURGICAL INSTRUMENTS WITH ROTATABLE BLADE AND HOLLOW SHEATH ARRANGEMENTS;

U.S. patent application Ser. No. 12/703,875, entitled ROTATABLE CUTTING IMPLEMENT ARRANGEMENTS FOR ULTRASONIC SURGICAL INSTRUMENTS;

U.S. patent application Ser. No. 12/703,879, entitled DUAL PURPOSE SURGICAL INSTRUMENT FOR CUTTING AND COAGULATING TISSUE;

U.S. patent application Ser. No. 12/703,885, entitled OUTER SHEATH AND BLADE ARRANGEMENTS FOR ULTRASONIC SURGICAL INSTRUMENTS;

U.S. patent application Ser. No. 12/703,893, entitled ULTRASONIC SURGICAL INSTRUMENTS WITH MOVING CUTTING IMPLEMENT; and U.S. patent application Ser. No. 12/703,899, entitled ULTRASONIC SURGICAL INSTRUMENT WITH COMB-LIKE TISSUE TRIMMING DEVICE.

Before explaining various embodiments of the ultrasonic surgical instruments in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof. It is also intended that any one or more of the following-described embodiments, expressions of embodiments, examples, can be combined with any one or more of the other following-described embodiments, expressions of embodiments, and examples.

Various embodiments are directed to improved ultrasonic surgical systems and instruments configured for effecting tissue dissecting, cutting, and/or coagulation during surgical procedures. In one embodiment, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy and the selective rotation of the cutting/coagulation implement.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

FIG. 1 illustrates in schematic form one embodiment of a surgical system 10 of the present invention. The surgical system 10 may include an ultrasonic generator 12 and an ultrasonic surgical instrument assembly 100 that may include a "self-contained" ultrasonic instrument 110. As will be discussed in further detail below, the ultrasonic generator 12 may be connected by a cable 14 to an ultrasonic transducer assembly 114 of the self-contained ultrasonic instrument 110 by a slip ring assembly 150 located in a housing portion 102 of the surgical instrument assembly 100. In one embodiment, the system 10 further includes a motor control system 20 that includes a power supply 22 that is coupled to a control module 24 by cable 23 to supply, for example, 24 VDC thereto. The motor control module 24 may comprise a control module manufactured by National Instruments of Austin, Tex. under Model No. NI cRIO-9073. However, other motor control modules may be employed. The power supply 22 may comprise a power supply manufactured by National Instruments. However, other power supplies may be successfully employed. The power supply 22 may be further coupled to a motor drive 26 by cable 25 to also supply 24 VDC thereto. The motor drive 26 may comprise a motor drive manufactured by National Instruments or others. Control module 24 may also be coupled to the motor drive 26 by cable 27 for supplying power thereto. A conventional foot pedal 30 or other control switch arrangement may be attached to the control module 24 by a cable 31. As will be discussed in further detail below, the ultrasonic surgical instrument 100 may include a motor 190 that has an encoder 194 associated therewith. As will be explained in further detail below, the motor 190 may be coupled to a torsional spring 300 which, in one embodiment, is coupled to the slip ring assembly 150. In one embodiment, the motor 190 may comprise a stepper motor manufactured by National Instruments under Model No. CTP12ELF10MAA00. The encoder 194 may comprise an encoder manufactured by U.S. Digital of Vancouver, Wash. under Model No. E2-500-197-I-D-D-B. However, other motors and encoders may be used. The encoder 194 may be coupled to the motor control module 24 by an encoder cable 32 and the motor 190 may be coupled to the motor drive 26 by cable 33. The surgical system 10 may also include a computer 40 that may communicate by Ethernet cable 42 with the motor control module 24.

As can also be seen in FIG. 1, in various embodiments, the motor control system 20 is housed in an enclosure 21. To facilitate easy portability of the system, various components may be attached to the motor control system 20 by removable cable connectors. For example, foot pedal switch 30 may be attached to a detachable cable connector 37 by cable 35 to facilitate quick attachment of the foot pedal to the control system 20. A/C power may be supplied to the power supply 22 by a conventional plug/cable 50 that is attached to a detachable cable connector 54 that is attached to cable 52. The computer 40 may have a cable 60 that is attached to detachable cable connector 62 that is coupled to cable 42. The encoder 194 may have an encoder cable 70 that is attached to a detachable connector 72. Likewise, the motor 190 may have a cable 74 that is attached to the detachable connector 72. The detachable connector 72 may be attached to the control module 24 by cable 32 and the connector 72 may be attached to the motor drive 26 by cable 33. Thus, cable connector 72 serves to couple the encoder 194 to the control module 24 and the motor 190 to the motor drive 26. The cables 70 and 74 may be housed in a common sheath 76.

In various embodiments, the ultrasonic generator 12 may include an ultrasonic generator module 13 and a signal generator module 15. See FIG. 1. The ultrasonic generator module 13 and/or the signal generator module 15 each may be integrated with the ultrasonic generator 12 or may be provided as a separate circuit modules electrically coupled to the ultrasonic generator 12 (shown in phantom to illustrate this option). In one embodiment, the signal generator module 15 may be formed integrally with the ultrasonic generator module 13. The ultrasonic generator 12 may comprise an input device 17 located on a front panel of the generator 12 console. The input device 17 may comprise any suitable device that generates signals suitable for programming the operation of the generator 12 in a known manner. Still with reference to FIG. 1, the cable 14 may comprise multiple electrical conductors for the application of electrical energy to positive (+) and negative (−) electrodes of an ultrasonic transducer assembly 114 as will be discussed in further detail below.

Various forms of ultrasonic generators, ultrasonic generator modules and signal generator modules are known For example, such devices are disclosed in commonly owned U.S. patent application Ser. No. 12/503,770, entitled Rotating Transducer Mount For Ultrasonic Surgical Instruments, filed Jul. 15, 2007, which is herein incorporated by reference in its entirety. Other such devices are disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

Figure 2:
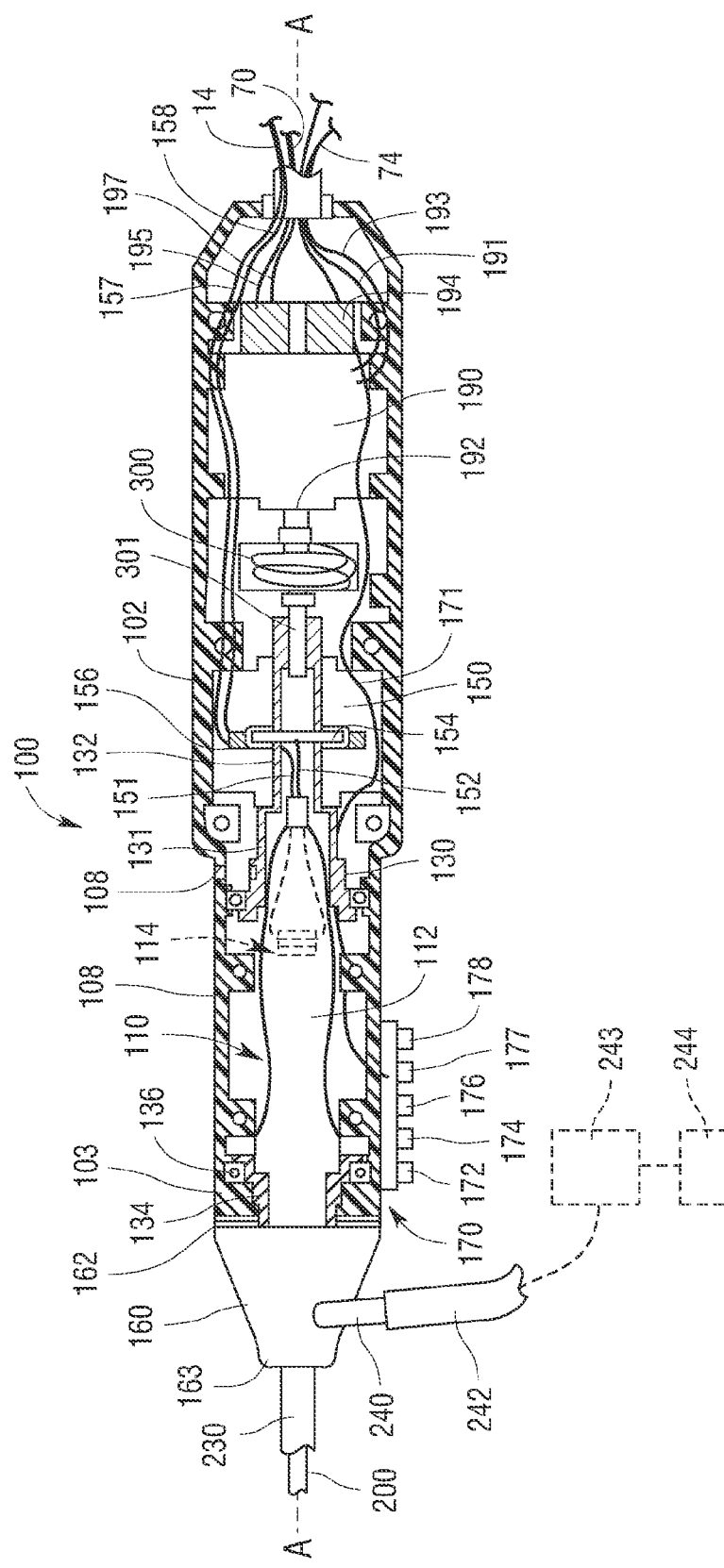
FIG. 2 is a cross-sectional view of a non-limiting handpiece embodiment of the present invention.

As can be seen in FIG. 2, an ultrasonic surgical instrument handpiece 100 may comprise a housing 102 that houses the motor 190, the encoder 194, the slip ring assembly 150 and the self-contained ultrasonic surgical instrument 110. The housing 102 may be provided in two or more parts that are attached together by fasteners such as screws, snap features, etc. and may be fabricated from, for example, polycarbonate, polyetherimide (GE Ultem®) or metals such as aluminum, titanium or steel. The motor 190 may comprise, for example, a stepper motor manufactured by National Instruments. However other motors may be employed to effectuate, for example, "gross" rotational motion of the self-contained ultrasonic surgical instrument 110 relative to the housing 102 on the order of 1-6000 rpm. The encoder 194 converts the mechanical rotation of the motor shaft 192 into electrical pulses that provide speed and other motor control information to the control module 24.

Figure 3:
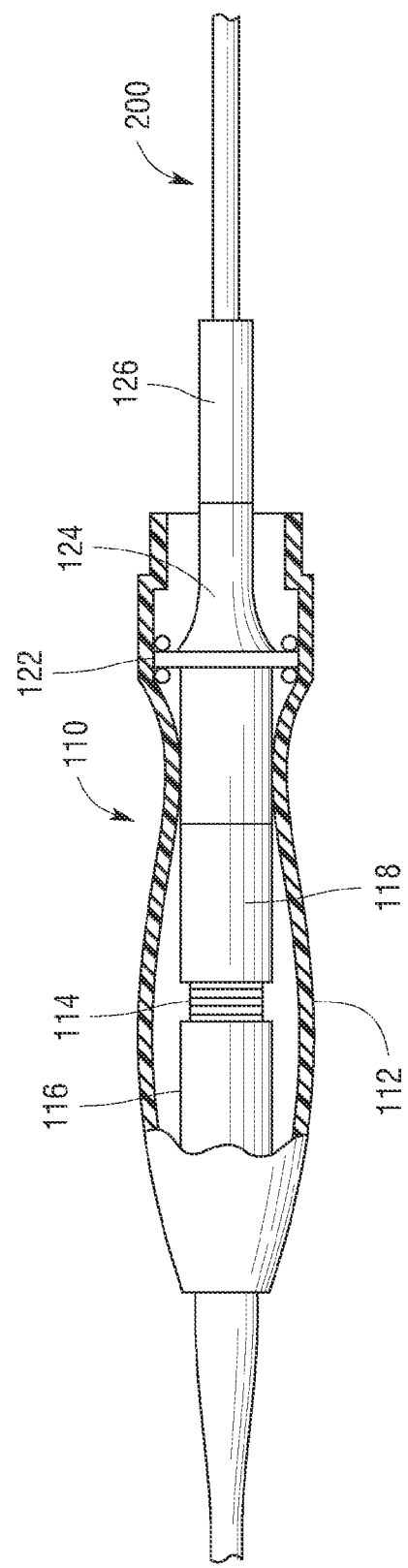
FIG. 3 is a partial cross-sectional view of an ultrasonic surgical handpiece that may be employed with various non-limiting embodiments of the present invention.

The self-contained ultrasonic surgical instrument 110 may comprise a surgical instrument that is manufactured and sold by Ethicon Endo-Surgery under Model No. HP054. However, other ultrasonic instruments may be successfully employed. It will be understood that the term "self-contained" as used herein means that the ultrasonic surgical instrument may be effectively used as an ultrasonic surgical instrument on its own, apart from use with the surgical instrument 100. As illustrated in more detail in FIG. 3, the ultrasonic surgical instrument 110 includes a housing 112 that supports a piezoelectric ultrasonic transducer assembly 114 for converting electrical energy to mechanical energy that results in longitudinal vibrational motion of the ends of the transducer assembly 114. The ultrasonic transducer assembly 114 may comprise a stack of ceramic piezoelectric elements with a motion null point located at some point along the stack. The ultrasonic transducer assembly 114 may be mounted between two cylinders 116 and 118. In addition, a cylinder 120 may be attached to cylinder 118, which in turn is mounted to the housing at another motion null point 122. A horn 124 may also be attached at the null point on one side and to a coupler 126 on the other side. A blade 200 may be fixed to the coupler 126. As a result, the blade 200 will vibrate in the longitudinal direction at an ultrasonic frequency rate with the ultrasonic transducer assembly 114. The ends of the ultrasonic transducer assembly 114 achieve maximum motion with a portion of the stack constituting a motionless node, when the ultrasonic transducer assembly 114 is driven at maximum current at the transducer's resonant frequency. However, the current providing the maximum motion will vary with each instrument and is a value stored in the non-volatile memory of the instrument so the system can use it.

The parts of the ultrasonic instrument 110 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the blade 200 of the acoustical mounting horn 124 decreases. Thus, the horn 124 as well as the blade/coupler may be shaped and dimensioned so as to amplify blade motion and provide ultrasonic vibration in resonance with the rest of the acoustic system, which produces the maximum back and forth motion of the end of the acoustical mounting horn 124 close to the blade 200. A motion from 20 to 25 microns at the ultrasonic transducer assembly 114 may be amplified by the horn 124 into blade movement of about 40 to 100 microns.

When power is applied to the ultrasonic instrument 110 by operation of the foot pedal 30 or other switch arrangement, the control system 20 may, for example, cause the blade 200 to vibrate longitudinally at approximately 55.5 kHz, and the amount of longitudinal movement will vary proportionately with the amount of driving power (current) applied, as adjustably selected by the user. When relatively high cutting power is applied, the blade 200 may be designed to move longitudinally in the range of about 40 to 100 microns at the ultrasonic vibrational rate. Such ultrasonic vibration of the blade 200 will generate heat as the blade contacts tissue, i.e., the acceleration of the blade 200 through the tissue converts the mechanical energy of the moving blade 200 to thermal energy in a very narrow and localized area. This localized heat creates a narrow zone of coagulation, which will reduce or eliminate bleeding in small vessels, such as those less than one millimeter in diameter. The cutting efficiency of the blade 200, as well as the degree of hemostasis, will vary with the level of driving power applied, the cutting rate or force applied by the surgeon to the blade, the nature of the tissue type and the vascularity of the tissue.

As can be seen in FIG. 2, the ultrasonic instrument 110 is supported within the housing 102 by a tailpiece drive adapter 130 and a distal handpiece adapter 134. The tailpiece drive adapter 130 is rotatably supported within housing 102 by a proximal bearing 132 and is non-rotatably coupled to the output shaft 192 of the motor 190. See FIG. 2. The tailpiece drive adapter 130 may be pressed onto the housing 112 of the ultrasonic instrument 110. The distal handpiece adapter 134 may be pressed onto a distal end 113 of the handpiece housing 112. The distal handpiece adapter 134 is rotatably supported in the housing 102 by a distal bearing 136 that is mounted within housing 102.

When power is applied to motor 190, motor 190 applies a "gross rotational motion" to the handpiece 110 to cause the ultrasonic surgical instrument 110 and blade 200 to rotate about central axis A-A. As used herein, the term "gross rotational motion" is to be distinguished from that "torsional ultrasonic motion" that may be achieved when employing in a non-homogeneous formed ultrasonic blade. The term "gross rotational motion" instead encompasses rotational motion that is not solely generated by operation of the ultrasonic transducer assembly 114.

To provide the ultrasonic instrument 110 with power from the ultrasonic generator 12, a slip ring assembly 150 may be employed. As can be seen in FIG. 2, conductors 151, 152 are coupled to the ultrasonic transducer assembly 114 and extend through a hollow stem portion 132 of the tail piece drive adapter 130. The hollow stem portion 132 is attached to a torsional spring 300 which is attached to the drive shaft 192 of the motor 190. The hollow stem portion 132 is free to rotate within the slip ring assembly 150. A first inner contact 154 is attached to the hollow stem portion 132 for rotational travel therewith about axis A-A. The first inner contact 154 is positioned for rotational contact with a fixed outer contact 156 within the slip ring assembly 150. The contacts 154, 156 may be provided in the form of concentrically arranged rings. Conductors 157, 158 are coupled to the fixed outer contact 156 and form generator cable 14. Conductors 191 and 193 are attached to the motor and form motor cable 74 and conductors 195, 197 are attached to encoder 194 and form encoder cable 70. Rotation of the motor shaft 192 results in the rotation of the tailpiece drive adapter 130 and the ultrasonic instrument 110 attached thereto about axis A-A. Rotation of the motor drive shaft 192 also results in the rotation of the inner contact 154. Ultrasonic signals from the ultrasonic generator 12 are transferred to the inner contact 154 by virtue of contact or "electrical communication" between the inner contact 154 and the outer contact 156. Those signals are transmitted to the ultrasonic transducer assembly 114 by conductors 151, 152.

As indicated above, various embodiments employ a torsional spring 300 that is mounted between the output shaft 192 of the motor 190 and a distal shaft segment 301 that is coupled to the tailpiece drive adapter 130. However, other torsional springs 300 may be employed. As used herein, the term "torsional spring" refers to those forms of springs that exert pressure along a path that is circular and should be distinguished from compression springs that exert forces in an axial direction. The purpose of torsional spring 300 will be explained below.

Various embodiments may also include a distal nosepiece 160 that may be removably attached to the distal end 103 of the housing 102 by fasteners 161. See FIG. 5. One or more shim members 162 may be positioned between the distal end 103 and the nosepiece 160 to facilitate coaxial attachment between the housing 102 and the nosepiece 160. The nosepiece 160 may be fabricated from, for example, polycarbonate, polyetherimide (GE Ultem®) or metals such as aluminum, titanium or steel. In various embodiments, the distal end 202 of the blade 200 extends through a hollow coupler segment 210 that is journaled within an inner sheath seal 212. Inner sheath seal 212 may serve to establish a substantially fluid-tight and/or airtight seal between the coupler segment 210 and the nosepiece 160. Also in the embodiment of FIG. 4, an inner sheath 220 may be attached to the hollow coupler segment 210 by, for example, a threaded connection or the hollow coupler segment 210 may comprise an integral portion of the inner sheath 220. In one embodiment, a blade pin/torquing member 216 may extend transversely through the blade member 200 and the hollow coupler segment 210 to facilitate movement of the inner sheath 220 with the blade member 200. One or more vented silicone bushings 214 may be journaled around the blade 200 to acoustically isolate the blade 200 from the inner sheath 220. The blade member 200 may have a proximal end 201 that is internally threaded and adapted to removably engage a threaded portion of the coupler 126. To facilitate tightening of the blade 200 to the coupler 126, a tightening hole 108 (FIG. 2) may be provided through the housing 102 to enable a tool (e.g., Allen wrench) to be inserted therethrough into a hole 131 in the tail piece drive adapter 130 to prevent the rotation of the ultrasonic surgical instrument 110 and coupler 126 attached thereto. Once the blade 200 has been screwed onto the coupler 126, the user may remove the Allen wrench or other tool from holes 108, 131 and insert a threaded plug (not shown) into hole 108 to prevent fluids/debris from entering the housing 102 therethrough.

Figure 4:
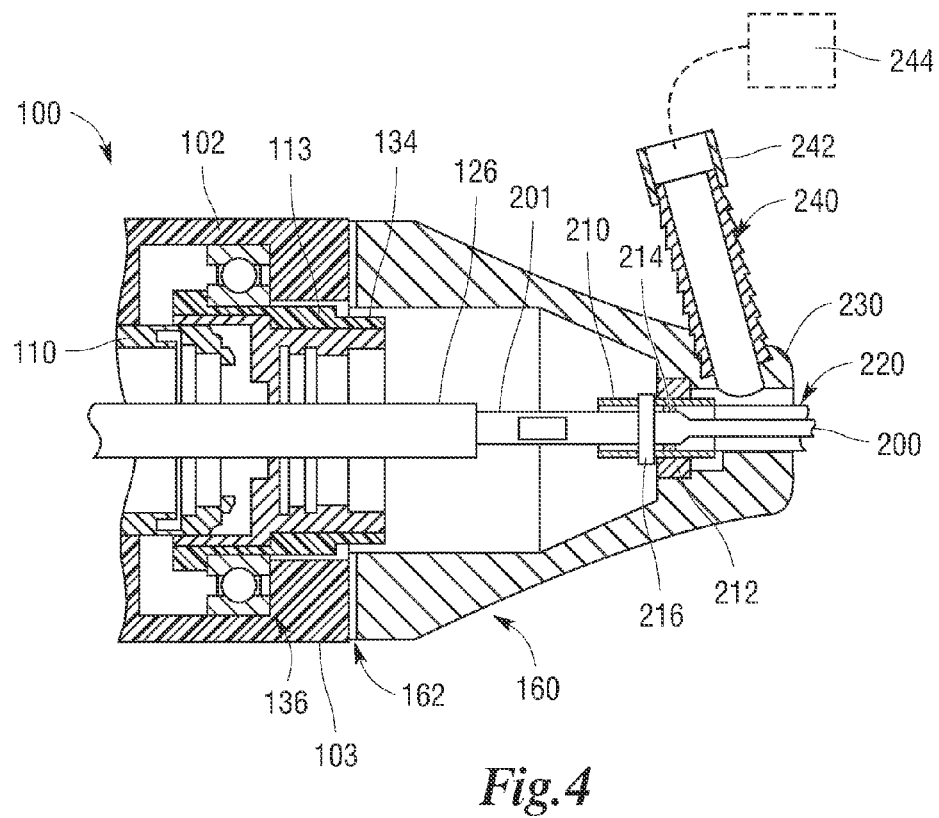
FIG. 4 is a cross-sectional view of a portion of a non-limiting nosepiece embodiment of the present invention.
Figure 5:
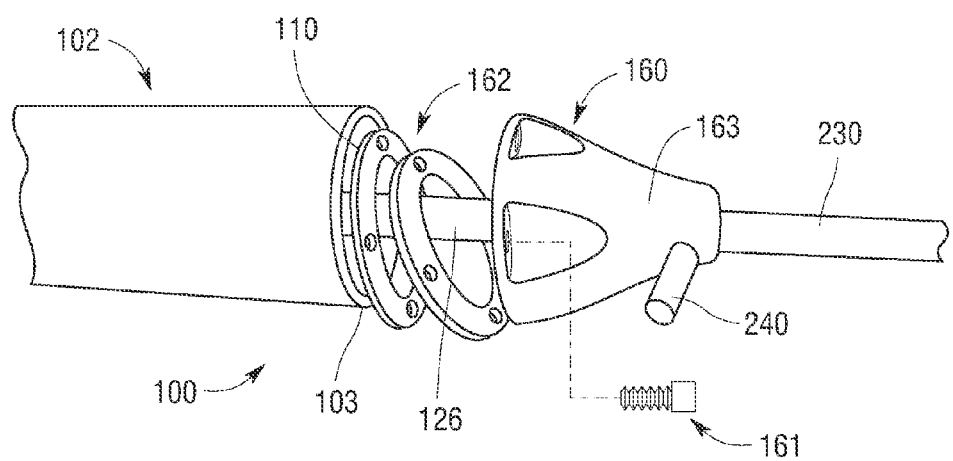
FIG. 5 is a partial exploded assembly view of a non-limiting nosepiece embodiment of the present invention.

Also in various embodiments, an outer sheath 230 may be coaxially aligned with the inner sheath 220 and blade member 200 and be attached to a distal end 163 of nosepiece 160 by, for example, welding or other suitable means. As can be seen in FIG. 4, a suction port 240 may be attached to the nosepiece 160 to communicate with the hollow outer sheath 230. A flexible tube 242 may be attached to the suction port 240 and communicate with a collection receptacle 243 that is coupled to a source of vacuum, generally depicted as 244. Thus, the outer sheath 230 forms a suction path extending around the inner sheath 220 that begins at a distal tip of the outer sheath 230 and goes out through the suction port 240. Those of ordinary skill in the art will appreciate that alternate suction paths are also possible. In addition, in alternative embodiments, the inner sheath 220 is omitted.

As can be seen in FIGS. 6 and 7, there is shown a distal tip portion 400 that may be attached to the distal end 231 of the outer sheath 230. In various embodiments, the outer sheath 230 may be fabricated from, for example, aluminum, titanium, aluminum alloys, steels, ceramics, etc. The distal tip portion 400 may be attached to the distal end 231 of the outer sheath 230 by, for example, welding, adhesive, etc. As shown in FIGS. 6 and 7, the distal tip portion 400 defines two cutting surfaces 402, 404 that form cutting board surfaces on each side of a blade opening 410 formed therein.

FIG. 8 illustrates one form of a distal tissue cutting tip 250 that is formed or otherwise provided on the blade 200. As can be seen in that Figure, the distal tissue cutting tip 250 has a pair of tissue cutting edges 252, 254 formed thereon. In various embodiments, the blade 250 may be fabricated from, for example, Titanium. In the embodiment depicted in FIGS. 6 and 7, a distal blade cap 260 may be attached to the distal end 251 of the distal tissue cutting tip 250 of the blade 200. The distal blade cap 260 may be sized to be rotatably supported within a tip cavity 412 formed in the distal tip portion 400 such that the blade 200 may oscillate back and forth (represented by arrow "38 B" in FIGS. 6 and 7) about longitudinal axis A-A Various embodiments of the surgical system 10 provide the ability to selectively apply ultrasonic motion to the blade 200 and gross rotational motion to the blade 200 as well. In some embodiments, for example, frequency ranges for longitudinal ultrasonic motion may be on the order of, for example, 30-80 kHz. In a preferred method of use, the blade 200 rotatably oscillates back and forth such that tissue is approximated between the cutting edges 252, 254 and the cutting surfaces 402, 404 (FIGS. 6 and 7). In various embodiments, tissue pads 270 fabricated from, for example, polytetrafluoroethylene or similar materials may be attached to the cutting surfaces 402, 404 by, for example, adhesives or other suitable fastener arrangements. Thus, the tissue may be approximated between the cutting edges 252, 254 and the cutting surfaces 402, 4040 or tissue pads 270. In use, the blade 200 and tissue may be momentarily both stopped, with the blade applying force to the tissue, and the pad 270 providing a "cutting board" surface on the apposing side. In various embodiments, the ultrasonically actuated blade 200 may act with a desired amount of pressure and time on the tissue. Thus, the computer processor 40 of the control system may be programmed to cause the motor 190 to stop after the blade 200 has trapped the tissue on the pad 270 for a predetermined dwell time. This would increase the amount of energy that is delivered to the tissue, thereby potentially improving the cutting speed or hemostatic effect. In various embodiments, dwell times in the range of 5 ms to 10 s may be successfully employed, for example. The ultrasonic transducer assembly 114 could be activated to provide ultrasonic motion to the blade prior to trapping the tissue or immediately after the tissue has been trapped between the cutting edge 252, 254 and the tissue pad 270.

During the cutting process, suction may be applied within the outer sheath 230 by the source of suction 244 such that the tissue is drawn in through the blade opening 410. As illustrated in FIGS. 8A-8C, when the blade 200 is in a central position as shown in FIG. 8A, tissue "T", "T'" can be drawn into both sides 410R, 410L of the blade opening 410. When the blade 200 oscillates to trap tissue "T" between cutting edge 252 and tissue pad 270 and is retained in that cutting position for the predetermined amount of dwell time, such dwell time allows other tissue "T'" to be drawn into the portion 410L of the blade opening 410 as shown in FIG. 8B. Similarly, when the blade 200 is oscillated to trap the tissue "T'" between the cutting edge 254 and tissue pad 270, and is retained in that position for the predetermined dwell time, other tissue "T" may be drawn into the portion 410R of the blade opening 410. It is believed that other devices that use a rotating blade for cutting tissue drawn into an opening in a sheath tend to "kick out" tissue as it is being drawn into the opening. The oscillating blade of various embodiments of the present invention is believed to be faster at cutting tissue than a continuously rotating one because when the blade is stopped, tissue has time to get drawn into an opposing side of the opening, thereby making it less likely to "kick out" when the blade is cutting.

Another unique and novel advantage provided by the present invention is the ability to control the amount of force that is generated at the blade/pad interface. For example, the embodiment described above employs the torsional spring in combination with the stepper motor and encoder to control the amount of force applied to the blade/ad interface. By controlling rotation of the motor past the blade/pad contact point results in the displacement or "loading" of the torsional spring by a certain angle that results in the application of a predetermined amount of torsional force to the blade. For example, Force=[Torsional Spring Rate]×[Angular Deflection]/[Distance Form Center of Rotation To Blade Edge]. Thus, in some non-limiting embodiments, for example, a preferred force would be in the range of 1.5 to 5 lbs. In an alternative embodiment, the motor 190 may comprise a servo motor and be used in connection with an appropriate encoder. In yet another embodiment, the torsional spring may be omitted and the motor output shaft 192 may be connected directly to the tailpiece drive adapter 130. In those embodiments, the motor 190 comprises a servo motor that generates the desired amount of torque based upon the applied current. In yet another embodiment, the control system would measure the amount of impedance in the motor circuit to control the oscillation speed. When engaged in tissue, the motor would draw a high load. Thus, in this embodiment, when the load exceeded a predetermined threshold, the motor could be slowed down to allow the ultrasonic blade to cut through the tissue.

Figure 9:
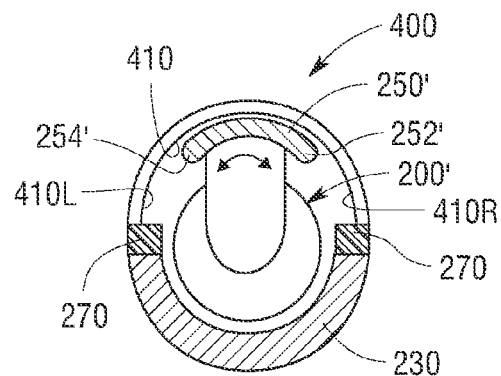
FIG. 9 is a partial cross-sectional end view of another non-limiting outer sheath and blade embodiment of the present invention.

FIG. 9 illustrates an alternative blade embodiment 200'. As can be seen in that Figure, the blade 200' has a distal tip 250' that is formed with a pair of blunt tissue cutting edges 252', 254'.

Figure 10:
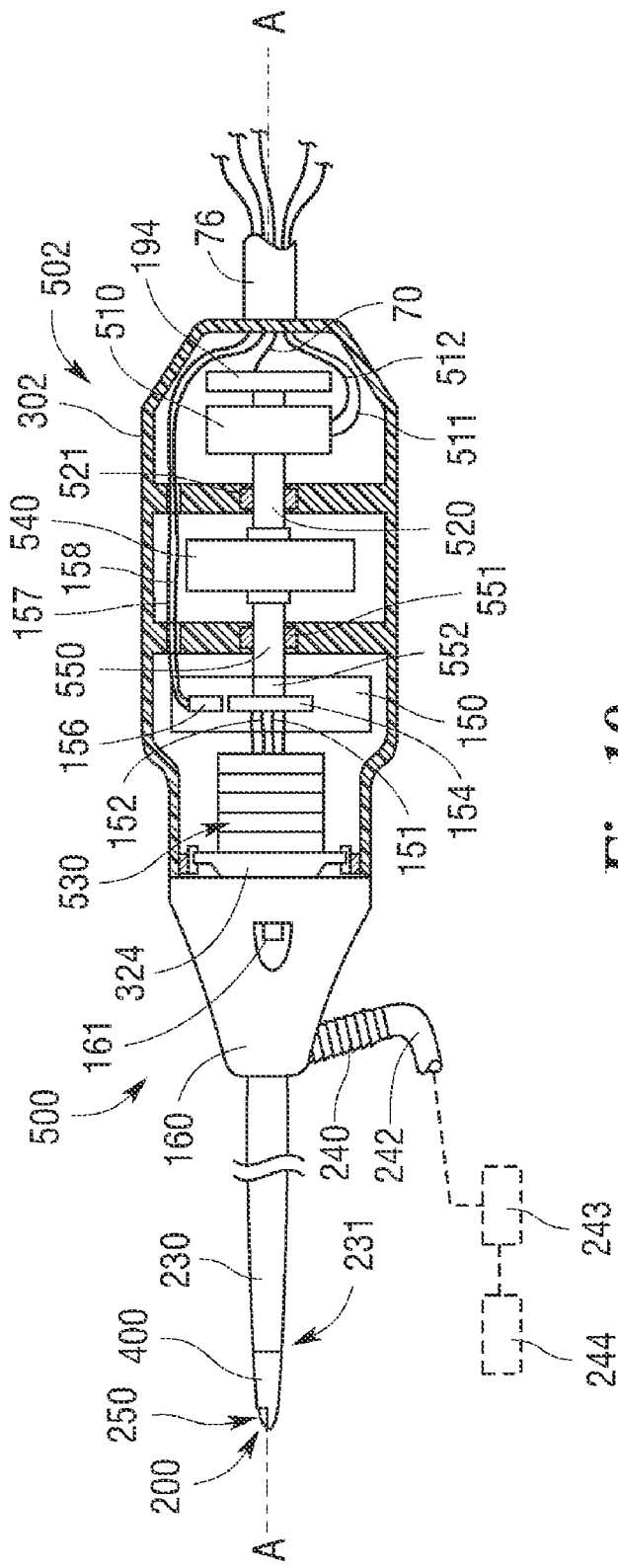
FIG. 10 is a partial side cross-sectional view of another non-limiting surgical instrument embodiment of the present invention.

FIG. 10 depicts another surgical instrument embodiment 500 of the present invention that employs a handpiece 502. In this embodiment, the handpiece 502 includes a housing 302 that houses a transducer assembly 530 that is attached to an ultrasonic horn 324. The ultrasonic horn 324 may be coupled to the proximal end 201 of the blade 200 by a threaded or other suitable connection. The ultrasonic horn 324 may be rotatably supported within the housing 302 by a distal bearing 336. A nosepiece 160 may be attached to the housing 302 in the manner described above.

This embodiment includes a motor 510 that may comprise a stepper motor of the type and construction described above and may have an encoder portion 194 associated therewith that communicates with the control module 24 (FIG. 1) through cable 70 as was described above. The motor 510 may receive power from the motor drive 26 (FIG. 1) through conductors 511, 512 that comprise motor cable 74 that extends through the common sheath 76. The motor 510 has an output shaft 520 that may be rotatably supported within the housing 302 by a first proximal bearing 521. The output shaft may be attached to a torsional spring 540. Attached to the torsional spring 540 is a hollow drive shaft segment 550 that may be rotatably supported within housing 302 by a second proximal bearing 551. A distal portion 552 of the drive shaft segment 550 extends through a slip ring assembly 150. The slip ring assembly 150 is fixed (i.e., non-rotatable) within the housing 302 and includes a fixed outer contact 156 that is coupled to conductors 157, 158 that form generator cable 14 (FIG. 1) as was described above. An inner contact 154 is mounted on the hollow drive shaft segment 550 and is in electrical contact or communication with outer contact 156. Conductors 151, 152 are attached to the inner contact 154 and extend through the hollow drive shaft 520 to be coupled to the ultrasonic transducer assembly 530.

This embodiment also employs an outer sheath 230 that may have a distal tip portion 400 attached to the distal end 231 thereof as was described above. The blade may have a distal tissue cutting tip 250 as was described above. When power is supplied to the motor 510, the drive shaft 520 rotates bout axis A-A which also causes the transducer assembly 530 to rotate about axis A-A. Because the blade 200 is attached to the horn 324, it too rotates with the ultrasonic transducer assembly 530. As was discussed above, the torsional spring 540 in combination with the stepper motor 510 and encoder 190 controls the amount of force applied to the blade/pad interface (i.e., the amount of torsion experienced by the tissue cutting portion of the blade when in contact with the cutting surface/pad).

When the clinician desires to power the ultrasonic transducer assembly 530, power is supplied from the ultrasonic generator 12 (FIG. 1) to the fixed contact 156 in the slip ring assembly 150. Power is transmitted to the ultrasonic transducer assembly 530 by virtue of rotational sliding contact or electrical communication between the inner contact 154 and the outer contact 156. Those signals are transmitted to the ultrasonic transducer assembly 530 by conductors 151, 152. Suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the distal tissue cutting tip 250 of the blade 200 to tissue as was discussed above. Thus, this embodiment may otherwise operate in the same manner as ultrasonic surgical instrument assembly 100 described above.

Figure 11:
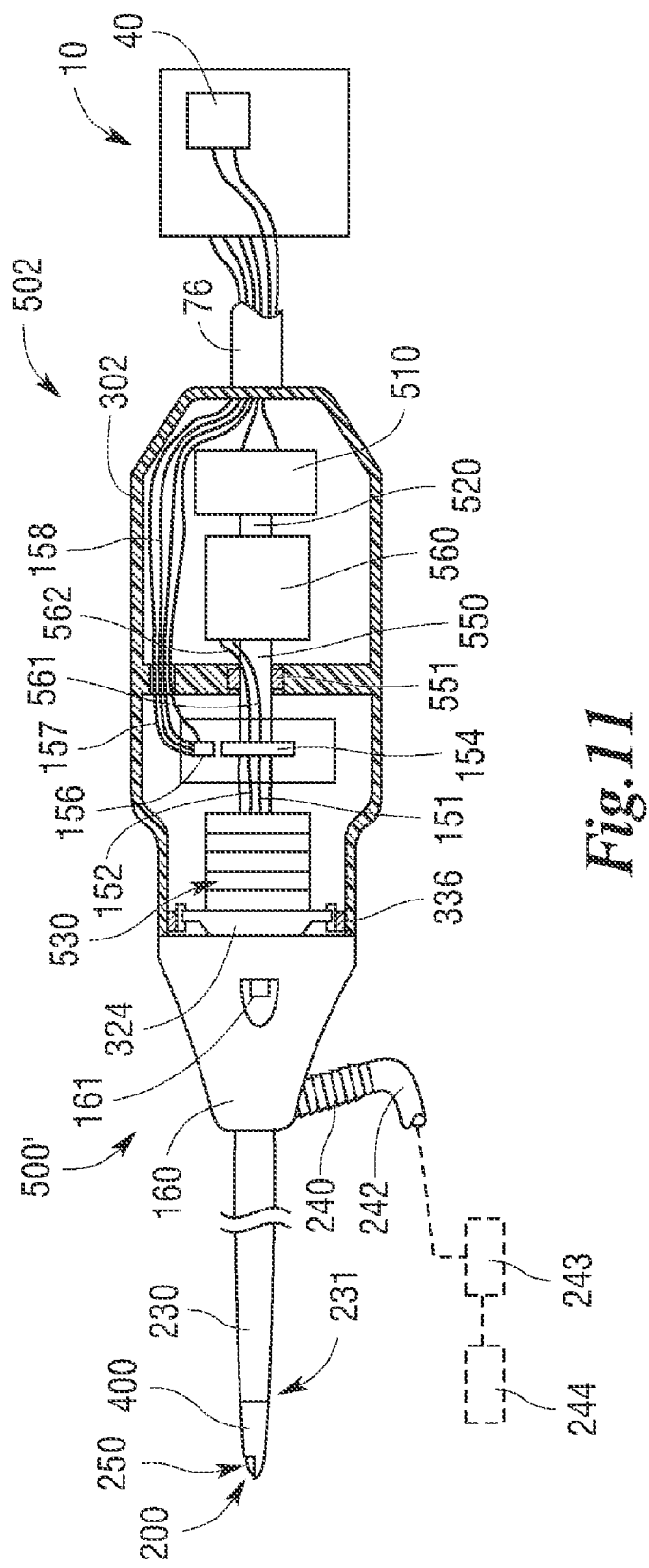
FIG. 11 is a partial side cross-sectional view of another non-limiting surgical instrument embodiment of the present invention.

FIG. 11 depicts an alternative surgical instrument embodiment 500' that is substantially similar in design and operation as the instrument 500 described above, except that this embodiment employs a torsional load cell 560 in place of the torsional spring 540 and encoder 194. For example, a torsional load cell of the type manufactured by Futek Advanced Technologies of Irvine, Calif. under Model No. TRD300 as well as others may be employed. As can be seen in FIG. 11, for example, the torsional load cell 560 may be attached to the output shaft 520 of the motor 510 as well as the hollow drive shaft segment 550. The torsional load cell 560 may communicate with the computer processor 40 by conductors 561, 562 in a known manner to enable the clinician to control the motor 510 based upon the amount of torque detected by the torsional load cell 560. Thus, the clinician may predetermine a desired amount of torque to be applied to the blade 200 and then program the computer processor to provide the appropriate motor control signals to the motor to maintain that level of torque.

Figure 13:
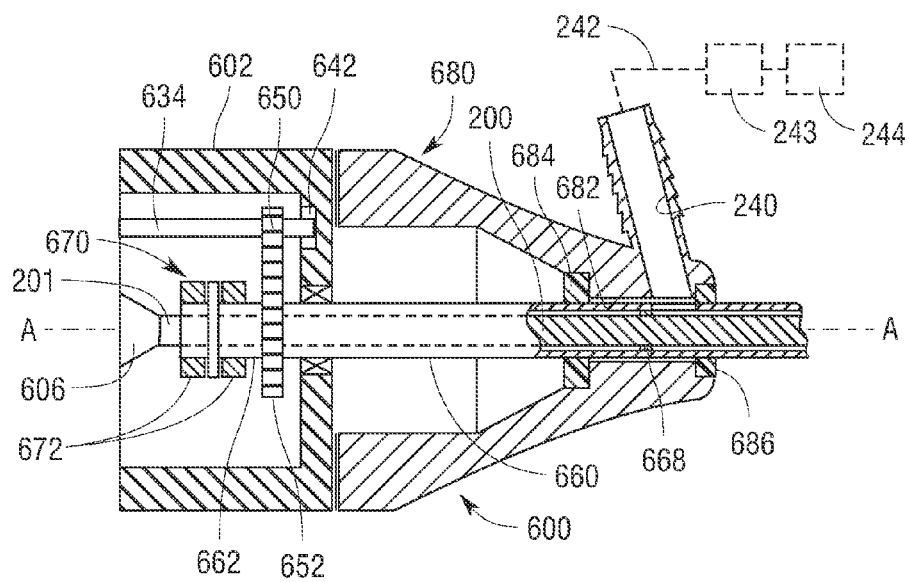
FIG. 13 is a cross-sectional view of a portion of a non-limiting nosepiece embodiment of the surgical instrument of FIG. 12.
Figure 12:
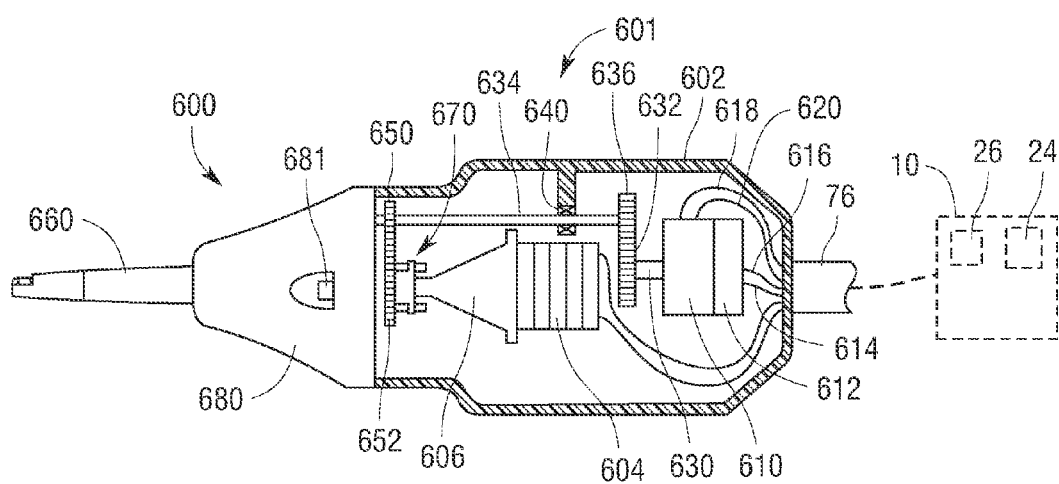
FIG. 12 is a partial side cross-sectional view of another non-limiting surgical instrument embodiment of the present invention.
Figure 16:
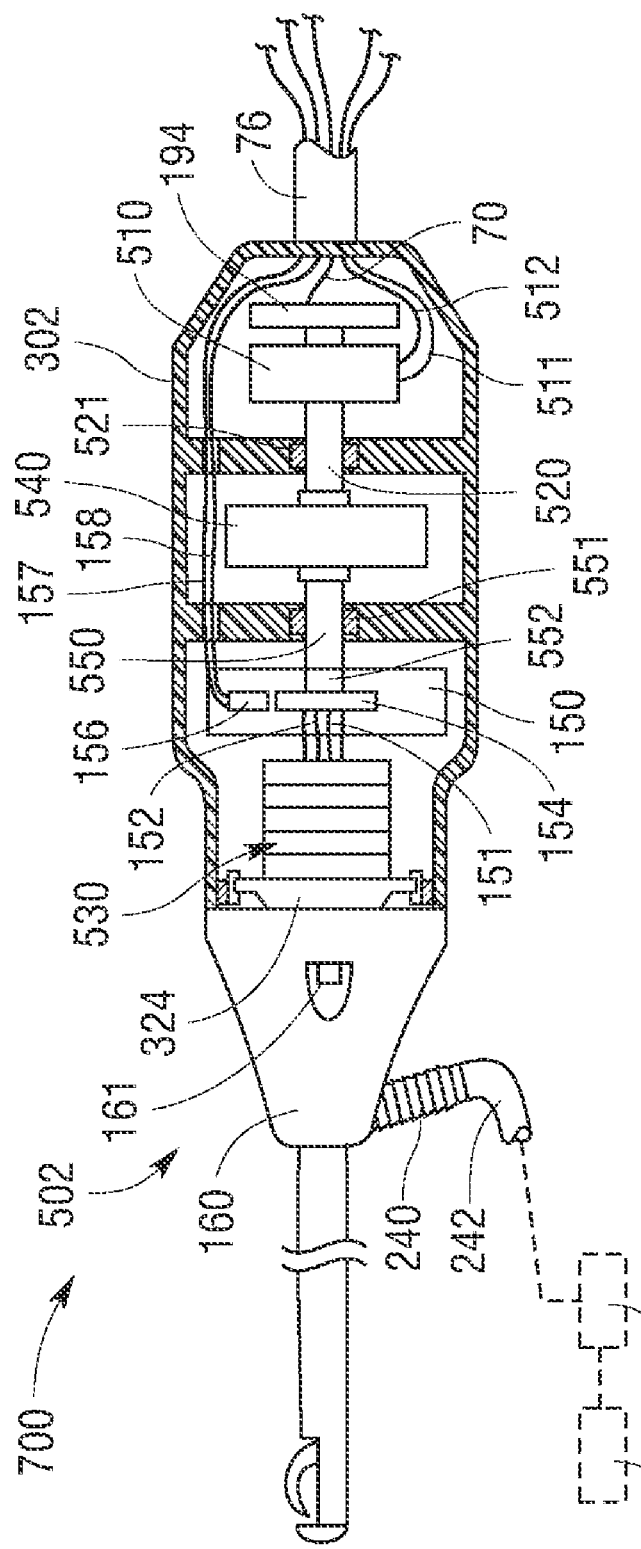
FIG. 16 is a partial side cross-sectional view of another non-limiting surgical instrument embodiment of the present invention.

FIGS. 12 and 13 depict another surgical instrument embodiment 600 of the present invention that employs a handpiece 601. In this embodiment, the surgical instrument 600 includes a handpiece 601 that includes a housing 602 that houses a transducer assembly 604 that is attached to an ultrasonic horn 606. The ultrasonic horn 606 may be coupled to the proximal end 201 of the blade 200 by a threaded or other suitable connection. In other embodiments, the blade 200 may be integrally formed with the horn 606. The ultrasonic transducer assembly 604 and the ultrasonic horn 606 are non-rotatably mounted within the housing 602.

This embodiment includes a motor 610 that may comprise a stepper motor of the type and construction described above and may have an encoder portion 612 associated therewith that communicates with the control module 24 through conductors 614, 616 in the manners described above. The motor 610 may receive power from the motor drive 26 through conductors 618, 620 that extend through the common sheath 76. The motor 610 is non-rotatably supported within the housing 602 and has an output shaft 630 that has a first drive gear 632 thereon. The first drive gear 632 is in meshing engagement with a second gear 636 that is mounted to a sheath drive shaft 634. The sheath drive shaft 634 may be supported in various bearing arrangements for rotation within the housing 602. In the embodiment depicted in FIGS. 12 and 13, the sheath drive shaft 634 is rotatably supported in a proximal bearing 640 and a distal bearing 642 (FIG. 13). A third drive gear 650 is attached to the distal end of the sheath drive shaft 634. The third drive gear 650 is in meshing engagement with a sheath gear 652 mounted to the proximal end portion 662 of an outer sheath 660 that rotatably extends around the blade 200 and is substantially coextensive therewith. As can be seen in FIG. 12, the proximal end 662 of the outer sheath 660 may have a flange 664 formed thereon that is rotatably received within a saddle portion 670 formed by cooperating standoffs 672 on the housing 602. Such arrangement prevents the outer sheath 660 from moving axially relative to the housing 602 while enabling the outer sheath 660 to rotate about axis A-A.

This embodiment also employs a nosepiece 680 that is somewhat similar to the nosepiece arrangement described above. The nosepiece 680 may be removably attached to the housing 602 by screws 681 or other suitable fastener arrangements. In this embodiment, the outer sheath 660 rotatably extends through a passage 682 in the nosepiece 680. Proximal seal 684 and distal seal 686 rotatably support the outer sheath 660 within passage 682 while establishing fluid tight seals therebetween. See FIG. 13. A suction port 240 may provided in the nosepiece 690 and communicates by means of a flexible tube 242 with a collection receptacle 243 that is coupled to a source of vacuum, generally depicted as 244. The outer sheath 660 is sized relative to the blade 200 so as to form a suction path 690 between the outer sheath 660 and the blade 200. At least one suction opening 664 is provided through the outer sheath 660 in the location of the suction port 240 such that as the outer sheath rotatably oscillates through a predetermined range of arcuate motion as will be discussed in further detail below, the suction opening 664 enables tissue pieces that are drawn between the outer sheath 660 and the blade 200 through passage 690 to exit the suction passage 690 out through opening 664 and port 240 to the collection receptacle 243. An internal seal 668 is also provided between the blade 200 and the rotating outer sheath 660 in a location that is proximal of the suction opening 664 as shown.

Figure 14:
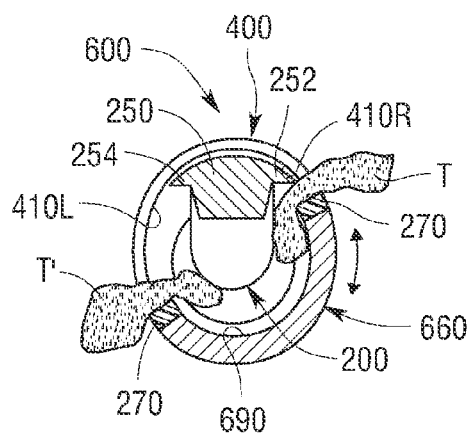
FIG. 14 is a partial cross-sectional end view of the outer sheath and blade arrangement of the surgical instrument of FIGS. 12 and 13 with the outer sheath in a tissue cutting position.
Figure 15:
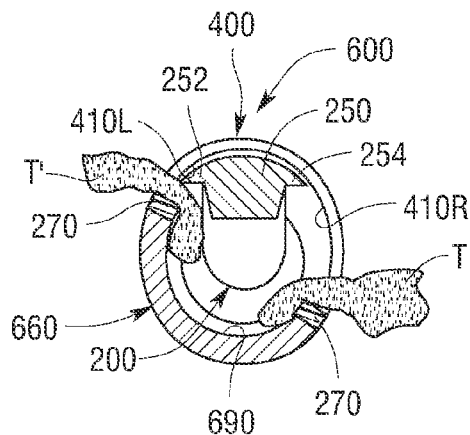
FIG. 15 is another partial cross-sectional end view of the outer sheath and blade arrangement of the surgical instrument of FIGS. 12 and 13 with the outer sheath in another tissue cutting position.

This embodiment may also employ the distal tip portion 400 of the type and construction described above as well as the distal cutting tip configurations 250, 250' as described above and illustrated in FIGS. 8 and 9. However, in this embodiment, the blade tip 250, 250' is stationary and the distal tip portion 400 (and the outer sheath 660) rotatably oscillate back and forth to cut tissue "T", "T"' between the cutting edges 252, 254. See FIGS. 14 and 15. The outer sheath 660 may be rotatably oscillated in any of the various manners described above by controlling the actuation of motor 610. As with the above-described embodiments, the outer sheath 660 may be rotatably oscillated to one cutting position and retained in that position for a predetermined dwell time. During the dwell time, other tissue may be drawn into the opposite side of the blade opening. After the dwell time has expired, the blade may rotatably oscillate to the other side of the blade opening to cut the other tissue during a similar dwell time, etc.

When the clinician desires to power the ultrasonic transducer assembly 530, power is supplied form the ultrasonic generator 12 (FIG. 1) to the fixed contact 156 in the slip ring assembly 150. Power is transmitted to the ultrasonic transducer assembly 530 by virtue of rotational sliding contact or electrical communication between the inner contact 154 and the outer contact 156. Those signals are transmitted to the ultrasonic transducer assembly 530 by conductors 151, 152. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the distal tissue cutting tip 250 of the blade 200 to tissue as was discussed above. Thus, this embodiment may otherwise operate in the same manner as ultrasonic surgical instrument assembly 100 described above.

FIGS. 16-26 depict another surgical instrument embodiment 700 of the present invention. This embodiment may employ a handpiece 502 of the type and construction described above as well as any of the variations employing a rotatably oscillating blade described above. In further alternative embodiments, those suitable handpieces disclosed in the following commonly owned U.S. patent applications that have been previously herein incorporated by reference may also be employed.

In various embodiments, the distal end 202 of the blade 200 may extend through a hollow coupler segment 210 that is journaled within an inner sheath seal 212. See FIG. 17. Inner sheath 220 may be attached to the hollow coupler segment 210 by, for example, a press fit, brazing, welding, epoxy, threads, etc. or the hollow coupler segment 210 may comprise an integral portion of the inner sheath 220. In one embodiment, a blade pin/torquing member 216 may extend transversely through the blade member 200 and the hollow coupler segment 210 to facilitate movement of the inner sheath 220 with the blade member 200. One or more vented silicone bushings 214 may be journaled around the blade 200 to acoustically isolate the blade 200 from the inner sheath 220. The blade member 200 may have a proximal end 201 that is internally threaded and adapted to removably engage a threaded portion of the coupler 126 in the various manners described above. In alternative embodiments, the proximal end 201 of the blade may be directly attached to the ultrasonic horn 324 or it may comprise an integral portion thereof.

Figure 18:
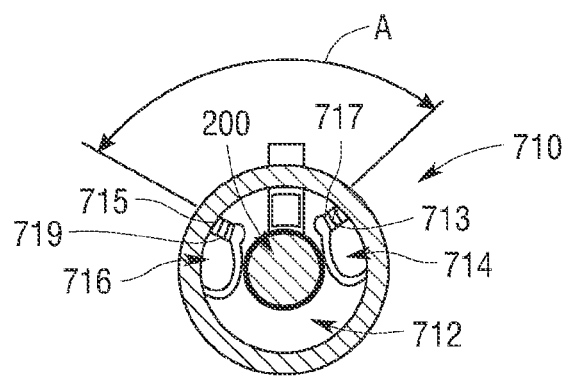
FIG. 18 is a cross-sectional view of the outer sheath and blade arrangement of the surgical instrument of FIGS. 16 and 17.
Figure 19:
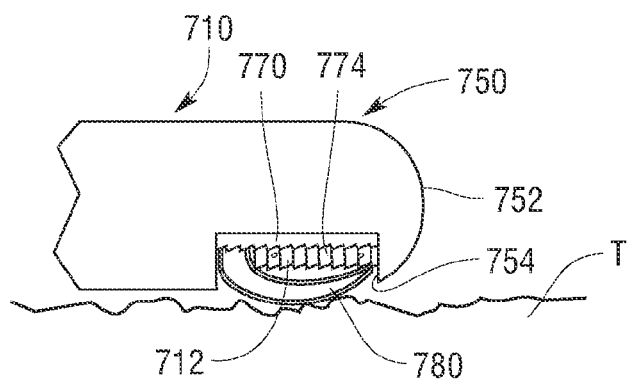
FIG. 19 is a side view of a portion of the blade and sheath arrangement of FIG. 18.
Figure 20:
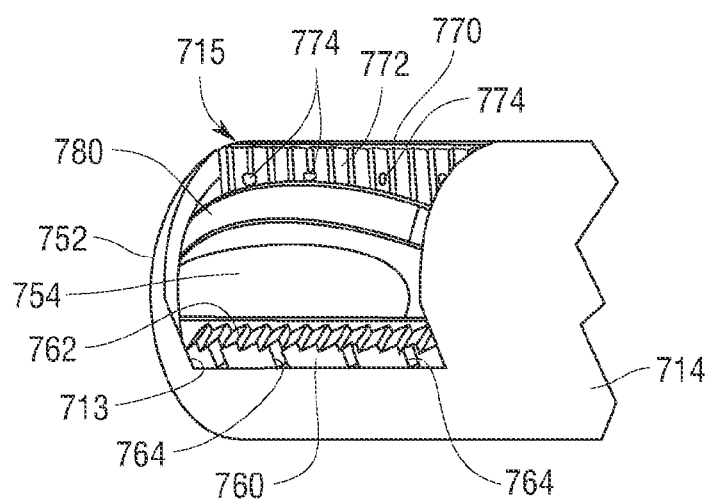
FIG. 20 is a perspective view of a portion of the blade and sheath arrangement of FIGS. 18 and 19.
Figure 21:
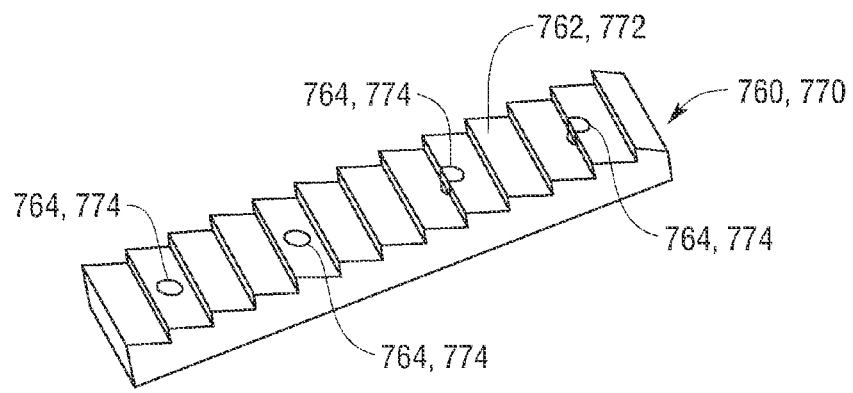
FIG. 21 is a perspective view of a non-limiting tissue pad embodiment of the present invention.

This embodiment may employ an outer sheath 710 that is fixed to the nosepiece 160. In various embodiments the outer sheath 710 may be fabricated from, for example, co-extruded polyimide or rolled welded metal and be attached to the nosepiece 160 by, for example, welding, adhesive, etc. The outer sheath 710 may be formed with a main lumen 712 and two pad lumens 714, 716 as illustrated in FIG. 18. As can be seen in FIGS. 19 and 20, the distal end 750 of the outer sheath 710 has a blunt end 752 and a blade opening 754 that communicates with the main lumen 712 through which the blade 200 extends. The first pad lumen 714 is defined by a first pad ledge 713 and the second pad lumen 716 is defined by a second pad ledge 715 as shown in FIG. 18. The first pad ledge 713 and the second pad ledge 715 are oriented relative to each other at an angle "A" as illustrated in FIG. 18. In the illustrated embodiment, angle "A" is approximately 135 degrees. As will be discussed below, angle "A" defines the arcuate path in which the blade 200 may travel. In other embodiments, angle "A" may have different magnitudes.

As can be seen in FIG. 20, a first tissue pad 760 may be attached to the first pad ledge 713 and a second tissue pad 770 may be attached to the second pad ledge 715. In various embodiments, the tissue pads 760, 770 may be fabricated from, for example, polytetrafluoroethylene or similar materials and have a serrated tissue gripping surface 762, 772 formed thereon. In alternative embodiments, the tissue surfaces 762, 772 may be flat. The pads 760, 770 may be attached to the pad surfaces 713, 715, respectively by, for example, interference fit, adhesives or mechanical fasteners. Pad 760 may have at least one vacuum port 764 therethrough that communicates with a corresponding first suction hole 717 that extends through the first pad surface 713 and into the first pad lumen 714. Likewise, the second tissue pad 770 may have at least one vacuum port 774 therethrough that communicates with a corresponding second suction hole 719 that extends through the second pad surface 715 and into the second pad lumen 716. Ports 764, 774 may be of any suitable geometry such as holes, stars, rectangular slits, plus signs, etc.

Figure 22:
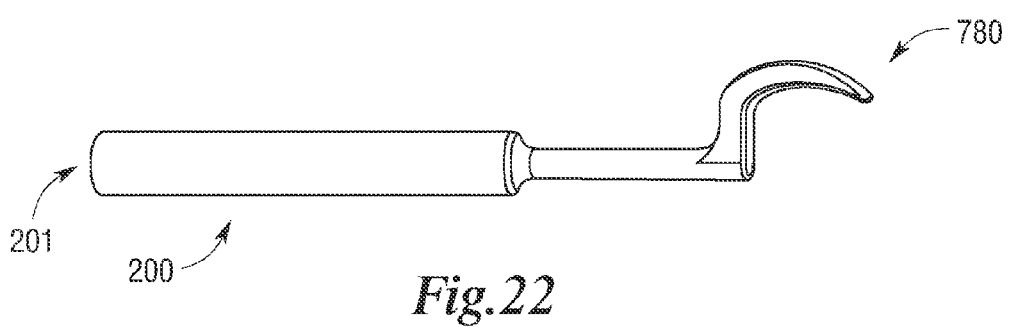
FIG. 22 is a side elevational view of a non-limiting blade embodiment of the present invention.

As can be seen in FIG. 22, the blade 200 has a proximal end 201 that may be attached to the coupler 126 in the various manners described above. In alternative embodiments, the blade 200 may be integrally formed with the ultrasonic horn. The blade 200 further has an arcuate tissue cutting portion 780 formed thereon. Other blade configurations could be employed. In various embodiments, the blade 200 may be fabricated from, for example, titanium, brass, aluminum or stainless steel.

Figure 17:
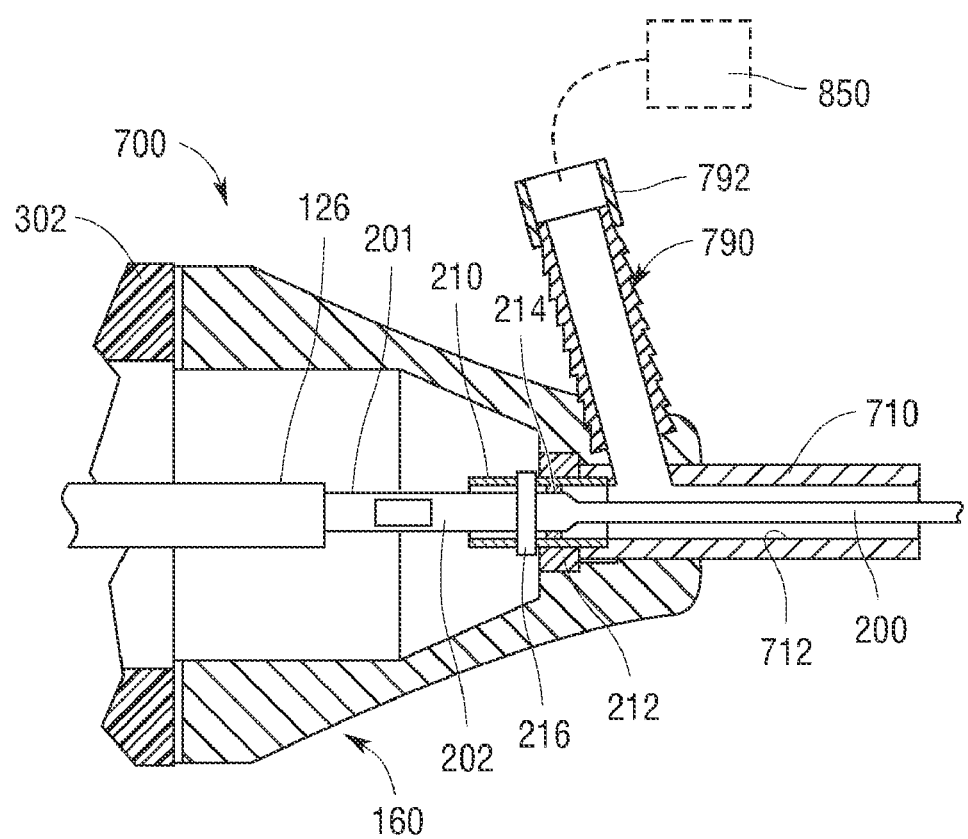
FIG. 17 is a cross-sectional view of a portion of a non-limiting nosepiece embodiment of the surgical instrument of FIG. 16.
Figure 23:
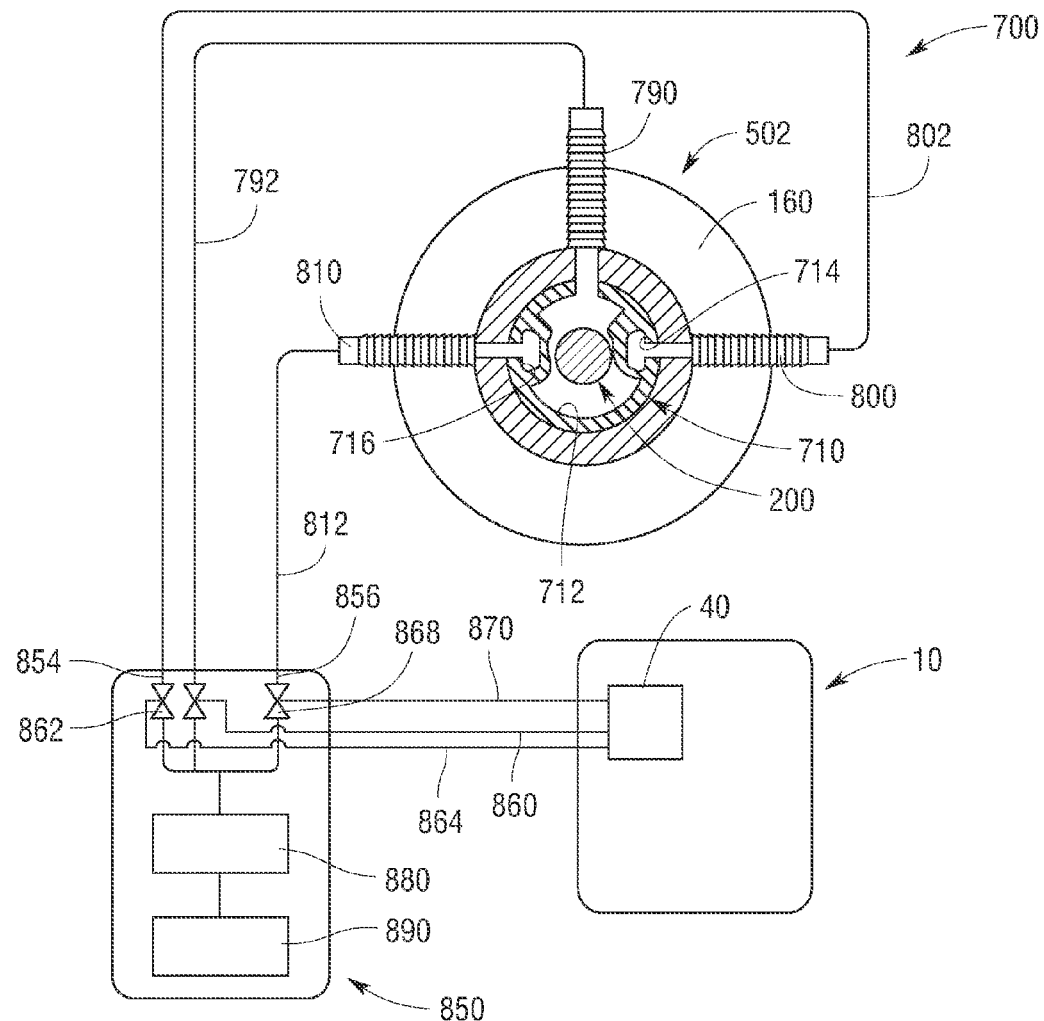
FIG. 23 is a cross-sectional end view of a portion of the surgical instrument of FIG. 16 with a suction control system embodiment and a portion of a control system embodiment of the present invention shown in schematic form.

As can be seen in FIGS. 17 and 23, a first suction port 790 may be attached to the nosepiece 160 and communicate with a suction control system 850 (FIG. 23) as will be further explained below. The first suction port 790 may communicate with the main lumen 712 to evacuate tissue and fluids therefrom through a flexible tube or hose 792 that is coupled to a first collection line 852 in the collection system 850. A second suction port 800 may be attached to the nosepiece 160 and communicate with the suction control system 850. The second suction port 800 may communicate with the first pad lumen 714 to provide suction thereto. The second suction port 800 communicates with a second collection line 854 in the collection system 850 by a second flexible tube or hose 802. A third suction port 810 may be attached to the nosepiece 160 and communicate with the suction control system 850. The third suction port 810 may communicate with the second pad lumen 716 to provide suction thereto. The second suction port 810 communicates with a third collection line 856 in the collection system 850 by a third flexible tube or hose 812.

As can be further seen in FIG. 23, a first control valve 858 is coupled between the first collection line 854 and the collection receptacle 880 which is coupled to a source of suction 890. The first control valve 858 may communicate with the computer controller 40 in the control system by first conductors 860. A second control valve 862 is coupled between the second collection line 854 and the collection, receptacle 880 and communicates with the computer controller 40 through conductors 864. A third control valve 868 is coupled between the third collection line 856 and the collection receptacle 880 and communicates with computer controller 40 through conductors 870.

Figure 24:
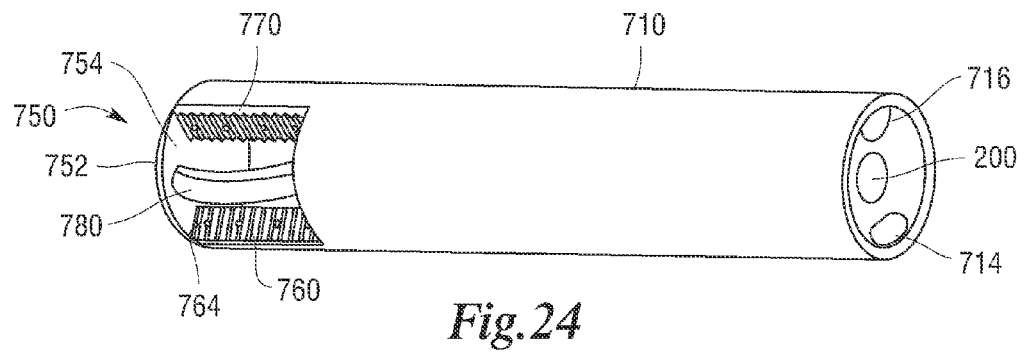
FIG. 24 is a perspective view of a portion of the blade and sheath arrangement of FIG. 23 with the blade in a first central position.
Figure 25:
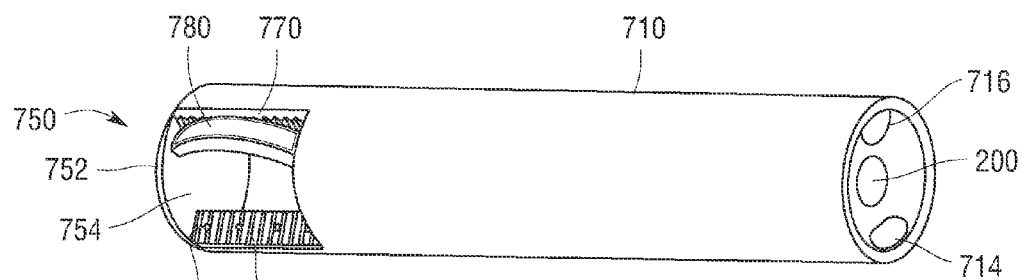
FIG. 25 is a perspective view of a portion of the blade and sheath arrangement of FIG. 24 with the blade in a tissue cutting position.
Figure 26:
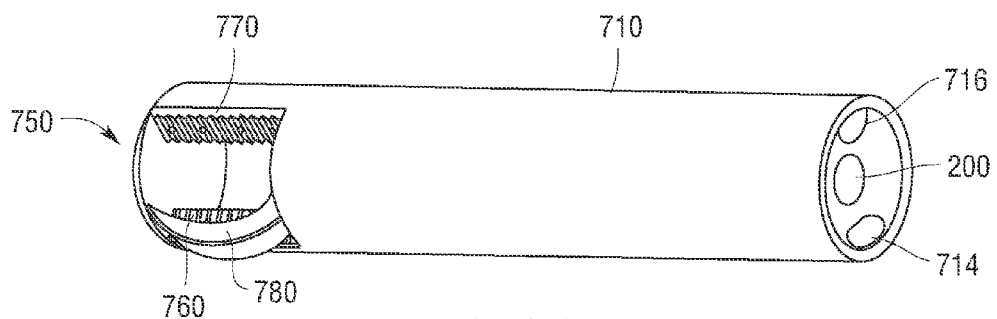
FIG. 26 is a perspective view of a portion of the blade and sheath arrangement of FIGS. 24 and 25 with the blade in another tissue cutting position.

FIGS. 24-26 illustrate one method of using the instrument 700. To commence use of the device, the distal end of the outer sheath 710 is inserted into the patient's body cavity with the tissue cutting portion 780 of the blade 200 positioned in the center of the window opening 754 as shown in FIG. 24. Thereafter, the clinician may activate the ultrasonic transducer assembly 530 (FIG. 16) through use of the foot pedal (FIG. 1) or other switching mechanism. The clinician may also activate the source of suction with all three control valves 858, 862, 868 in an open position to apply suction to the main lumen 712 and first and second pad lumens 714, 716. In a preferred embodiment, only one of the control valves 862, 868 for the pad lumens 714, 716 are opened at a time, however, as will be further discussed below. The clinician may then bring the distal end 750 of the outer sheath 710 into contact with target tissue to enable the target tissue to be drawn onto one or both of the tissue pads 760, 770. The tissue fibrils will be held in place on the tissue pads 760, 770 by the vacuum through the suction ports 764, 774. The clinician may then activate the motor 510 (FIG. 16) to rotate the blade 200 such that the tissue cutting portion 780 thereof is rotated onto the tissue on one of the tissue pads 760, 770. FIG. 25 illustrates the tissue cutting portion 780 rotated to a position adjacent to the second tissue pad 770 with the tissue omitted for clarity. The control system 10 automatically or the clinician may manually retain the tissue cutting portion 780 in that position for a predetermined dwell time to ensure transection of the fibrils/tissue. The dwell time may be, for example, approximately three (3) seconds. However, other dwell times may be employed and may be dependent upon the types of tissue to be transected.

Once the dwell time has expired, the suction is discontinued to the pad lumen that the tissue cutting portion 780 of the blade 200 is in contact with. In the example depicted in FIG. 25, the control valve 868 will be moved to a venting position wherein the suction line 812 as well as the pad lumen 716 are vented to atmosphere. This may be automatically accomplished by the control system 10 or through manual switches (not shown) coupled to the control valve 868. The tissue cutting portion 780 may then be returned to the central position illustrated in FIG. 24 by activating the motor 510. This may be automatically accomplished by control system 10 or through manual activation of manual switches (not shown) by the clinician. By rotating the tissue cutting portion 780 of the blade 200 to the central position and discontinuing the suction to the pad lumen 716 will enable any tissue debris remaining on the tissue pad 770 to be sucked through the main lumen 712. The control system may retain the blade tip 780 in the central position for a second predetermined dwell time to provide time for the tissue debris to be evacuated out through the main lumen 712, line 792, line 852, valve 858 and into the collection receptacle 880. Thereafter, once the second dwell time has expired, the control system may open control valve 862 to apply suction to pad lumen 714. In other embodiments, once the clinician observes that the pad 770 is clear from tissue debris, the clinician may then open control valve 862 by manually activating a switch (not shown).

When suction is applied to the pad lumen 714, tissue will be drawn onto the pad 760. The tissue cutting tip 780 may then be rotated onto that tissue on pad 760 as shown in FIG. 26. The control system 10 automatically or the clinician may manually retain the tissue cutting portion 780 in that position for a third predetermined dwell time to ensure transection of the fibrils/tissue. The third dwell time may be, for example, approximately three (3) seconds. However, other third dwell times may be employed and may be dependent upon the types of tissue to be transected.

Once the third dwell time has expired, the suction is discontinued to the pad lumen 760. This may be accomplished by moving the control valve 862 to a venting position wherein the suction line 802 as well as the pad lumen 714 are vented to atmosphere. This may be automatically accomplished by the control system 10 or through manual switches (not shown) coupled to the control valve 862. The tissue cutting portion 780 of the blade 200 may then be returned to the central position illustrated in FIG. 24 by activating the motor 510. This may be automatically accomplished by control system 10 or through manual activation of manual switches (not shown) by the clinician. By rotating the tissue cutting portion 780 of the blade 200 to the central position and discontinuing the suction to the pad lumen 714 will enable any tissue debris remaining on the tissue pad 760 to be sucked through the main lumen 712. The control system may retain the blade tip 780 in the central position for a second predetermined dwell time to provide time for the tissue debris to be evacuated out through the main lumen 712, line 792, line 852, valve 858 and into the collection receptacle 880. Thereafter, once that dwell time has expired, the control system may repeat the above-described processes until the desired amount of tissue has been transected.

In various embodiments, the blade 200 is rotated back and forth quickly (e.g., twenty (20) revolutions per minute (RPM's), to achieve cutting speeds that may be comparable to the cutting speeds commonly achieved when using current mechanical systems. In addition, however the various embodiments of the present invention provide the added advantage of hemostasis. For example, if a bleeder is encountered, the tissue cutting tip 780 of the blade 200 could be held stationary in the center of the window 754 while it is activated (i.e., receiving ultrasonic motion from the transducer assembly 530) and then be applied to the bleeder to cause hemostasis. The blade tip 780 could be rubbed over the area of the bleeder and ablate the tissue.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

All of the above U.S. patents and U.S. patent applications, and published U.S. patent applications referred to in this specification are incorporated herein by reference in their entirety, but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument, comprising:
   a housing;
   an outer sheath supported by said housing and protruding therefrom, said outer sheath having a distal blade opening therein that defines at least one cutting surface, said outer sheath having at least one suction lumen therethrough that communicates with said distal blade opening;
   an ultrasonic transducer assembly supported by said housing;
   a blade coupled to said ultrasonic transducer assembly and extending through said outer sheath such that a distal tip of said blade extends into said distal blade opening and wherein a tissue cutting portion thereof protrudes radially out of said distal blade opening; and
   a motor supported by said housing and coupled to one of said ultrasonic transducer assembly and said outer sheath for applying rotational motion thereto such that said tissue cutting portion of said blade is brought into contact with said at least one cutting surface on said outer sheath.

2. The ultrasonic surgical instrument of claim 1 further comprising a tissue pad attached to each said at least one cutting surface.

3. The ultrasonic surgical instrument of claim 2 wherein each said tissue pad has a tissue gripping surface thereon.

4. The ultrasonic surgical instrument of claim 1 wherein said at least one suction lumen comprises:
   a main suction lumen extending through said outer sheath; and
   a pad lumen extending through said outer sheath and communicating with at least one suction hole through a corresponding one of said at least one cutting surfaces.

5. The ultrasonic surgical instrument of claim 4 further comprising a tissue pad on said corresponding one of said at least one cutting surfaces and having another suction hole communicating with a corresponding one of said at least one suction hole through said cutting surface.

6. The ultrasonic surgical instrument of claim 1 wherein said at least one cutting surface comprises:
   a first cutting surface on one lateral side of said blade opening; and
   a second cutting surface on another lateral side of said blade opening and wherein said application of rotational motion to one of said ultrasonic transducer and said outer sheath brings said tissue cutting portion of said blade into contact with each of said first and second cutting surfaces.

7. The ultrasonic surgical instrument of claim 6 further comprising a tissue pad on each of said first and second cutting surfaces.

8. The ultrasonic surgical instrument of claim 6 wherein said at least one suction lumen comprises:
   a first a pad lumen extending through said outer sheath and communicating with at least one first suction hole through said first cutting surface;
   a second pad lumen extending through said outer sheath and communicating with at least one second suction hole through said second cutting surface; and
   a main suction lumen extending through said outer sheath and communicating with said blade opening.

9. The ultrasonic surgical instrument of claim 8 further comprising a suction control system communicating with said first and second pad lumens and said main suction lumen.

10. The ultrasonic surgical instrument of claim 9 wherein said suction control system comprises:
    a source of suction;
    a collection receptacle communicating with said source of suction;
    a first suction supply line coupled to said collection receptacle and said first pad lumen;
    a second suction supply line coupled to said collection receptacle and said second pad lumen;
    a main suction supply line coupled to said collection receptacle and said main suction lumen;
    a first valve in said first suction supply line;
    a second valve in said second suction supply line; and
    a third valve in said main suction supply line.

11. The ultrasonic surgical instrument of claim 6 wherein said tissue cutting portion of said blade has a first tissue cutting edge corresponding to said first cutting surface and a second tissue cutting edge corresponding to said second cutting surface.

12. The ultrasonic surgical instrument of claim 11 wherein said first and second tissue cutting edges are blunt edges.

13. The ultrasonic surgical instrument of claim 1 wherein said distal tip of said blade has an arcuate shape.

14. A method of cutting tissue, comprising:
    inserting a blade of a surgical instrument into a patient wherein the blade is attached to a source of ultrasonic motion and extends through a hollow outer sheath wherein a tissue cutting tip of the blade is exposed through a blade opening in the outer sheath and wherein one of the blade and outer sheath is selectively rotatable relative to the other;
    positioning the blade and outer sheath such that the blade opening is adjacent to target tissue within the patient;
    applying suction through the outer sheath to draw target tissue into the blade opening; and
    an oscillating one of the blade and outer sheath relative to the other such that the tissue cutting tip of the blade contacts and traps a portion of the target tissue drawn into the blade opening between the cutting tip and a cutting surface on the outer sheath.

15. The method of claim 14 further comprising retaining the cutting tip of the blade in contact with the target tissue trapped between the cutting tip and the cutting surface for a predetermined dwell time.

16. The method of claim 15 further comprising rotating one of the blade and outer sheath relative to the other upon expiration of said dwell time to contact and trap other tissue between the cutting tip of the blade and another cutting surface on the outer sheath.

17. An ultrasonic surgical instrument, comprising:
    a housing;
    an outer sheath supported by said housing and protruding therefrom, said outer sheath having a distal blade opening therein that defines at least one cutting surface;
    an ultrasonic transducer assembly rotatably supported by said housing;
    a blade coupled to said ultrasonic transducer assembly and extending through said outer sheath such that a distal tip of said blade extends into said blade opening wherein a tissue cutting portion thereof protrudes radially out of said blade opening;
    a motor supported by said housing and coupled to said ultrasonic transducer assembly for applying rotational motion thereto such that said tissue cutting portion of said blade is brought into contact with said at least one cutting surface; and
    means for limiting an amount of torsion experienced by said tissue cutting portion of said blade when in contact with said cutting surface.

18. The ultrasonic surgical instrument of claim 17 wherein said means for limiting comprises a torsional spring operably coupled to said motor and said ultrasonic transducer assembly.

19. The ultrasonic surgical instrument of claim 17 wherein said means for limiting comprises a torsional load cell operably coupled to said motor and said ultrasonic transducer.

20. The ultrasonic surgical instrument of claim 17 wherein said motor comprises a stepper motor with an encoder operably coupled thereto.

* * * * *